United States Patent
Crocker et al.

(10) Patent No.: US 11,974,776 B2
(45) Date of Patent: May 7, 2024

(54) ARTHROSCOPIC INTRODUCTION SYSTEM

(71) Applicant: Nexus CMF, L.L.C., Salt Lake City, UT (US)

(72) Inventors: Kevin Crocker, Cottonwood Heights, UT (US); Ben Himes, Salt Lake City, UT (US)

(73) Assignee: Nexus CMF, L.L.C., Salt Lake City, UT (US)

( * ) Notice: Subject to any disclaimer, the term of this patent is extended or adjusted under 35 U.S.C. 154(b) by 90 days.

(21) Appl. No.: 17/320,020

(22) Filed: May 13, 2021

(65) Prior Publication Data
US 2022/0361914 A1 Nov. 17, 2022

(51) Int. Cl.
*A61B 17/34* (2006.01)
*A61B 17/32* (2006.01)
*A61B 90/00* (2016.01)

(52) U.S. Cl.
CPC .. *A61B 17/3423* (2013.01); *A61B 17/320016* (2013.01); *A61B 17/3478* (2013.01); *A61B 90/06* (2016.02); *A61B 2090/062* (2016.02)

(58) Field of Classification Search
CPC ............... A61B 17/3423; A61B 90/06; A61B 17/320016; A61B 17/3478; A61B 2090/062; A61B 2017/320052
See application file for complete search history.

(56) References Cited

U.S. PATENT DOCUMENTS

| | | | |
|---|---|---|---|
| 5,954,671 A * | 9/1999 | O'Neill | A61B 17/1637 606/179 |
| 2003/0083689 A1* | 5/2003 | Simonson | A61M 29/00 606/191 |
| 2006/0064101 A1* | 3/2006 | Arramon | A61B 17/32002 606/82 |
| 2011/0087261 A1* | 4/2011 | Wittkampf | A61B 17/3478 606/185 |
| 2019/0008551 A1* | 1/2019 | Entabi | A61B 17/3415 |

* cited by examiner

*Primary Examiner* — Zade Coley
*Assistant Examiner* — Diana Jones
(74) *Attorney, Agent, or Firm* — Bryant J. Keller; Kirton McConkie

(57) ABSTRACT

An arthroscopic port introduction system includes an elongate hollow introducing needle and an elongate stylet sized and adapted to be disposed within the elongate hollow introducing needle together forming a single tissue-penetrating tip. The system also includes an elongate hollow enlarging shaft adapted to be disposed over the elongate hollow introducing needle. An operative tissue-penetrating length of the elongate hollow introducing needle is exposed beyond a distal end of the elongate hollow enlarging shaft. The elongate hollow introducing needle can be removed in a proximal direction from the elongate hollow enlarging shaft. An arthroscopic port sheath is disposed over the elongate hollow enlarging shaft and an operative tissue-penetrating length of the elongate hollow enlarging shaft is exposed beyond a distal end of the arthroscopic port sheath. The elongate hollow enlarging shaft can be removed in a proximal direction from the arthroscopic port sheath.

22 Claims, 29 Drawing Sheets

ARTHROSCOPIC INTRODUCTION SYSTEM

BACKGROUND OF THE INVENTION

1. Field of the Invention

The present invention relates to arthroscopy, and more particularly to arthroscopic introduction systems facilitating placement of arthroscopes during procedures.

2. Background and Related Art

In some arthroscopic procedures, proper placement of the arthroscope can be difficult. While proper placement can be particularly difficult for less-skilled practitioners, in some arthroscopic procedures, such as those involving small joint spaces such as the temporomandibular joint (TMJ) space, proper placement can even be difficult for even practiced practitioners at times. Proper placement can be difficult due to considerations such as access, size of the joint space, lack of visualization, or other concerns.

Difficulty in placement can cause significant difficulties for the practitioner and can result in injury to the patient as the practitioner attempts to achieve proper placement. Injuries to the patient can include injury from multiple attempts to penetrate the joint space, as well as injuries due to over-penetration. Depending on the joint space (e.g., the TJM space), over-penetration injuries are of particular concern.

One of the causes of difficulty in arthroscopic placement is the relatively small size of the access location of the joint relative to the diameter of the arthroscope. Unfortunately, the diameter of the arthroscope cannot be diminished; if the arthroscope diameter were diminished there would be insufficient room within the arthroscope for introduction of the necessary arthroscopic tools and/or scopes. Accordingly, any system that facilitates proper placement of arthroscopes would be a welcome improvement.

BRIEF SUMMARY OF THE INVENTION

Implementation of the invention provides devices, systems, and methods for placing and introducing an arthroscopic port into an arthroscopic space, such as within a joint space. By way of example, a joint space that may be accessed using implementation of the invention may be a temporomandibular joint (TMJ) space, such as, for example, the superior compartment or the inferior compartment, and more specifically, for example, the posterior recess of the superior compartment of the TMJ or the anterior recess of the superior compartment of the TMJ. Implementation of the invention greatly facilitates proper placement of an access port or arthroscopic port sheath that permits arthroscopic instruments such as cameras, surgical tools, and the like to access the joint space and be used in performing arthroscopic surgical procedures and the like.

While there can be great difficulty in properly placing relatively large-bore access ports in the correct joint space in arthroscopic procedures using traditional methods and systems, even after exploratory placement of smaller-bore needles and the like, implementation of the invention greatly facilitates proper placement and addresses the difficulty. Implementation of the invention allows initial proper placement of a relatively small-bore inner needle, followed by advancement of progressively larger-bore devices while the smaller-bore parts of the system remain in place, guaranteeing proper placement of the larger-bore devices. Once the arthroscopic port sheath is properly placed, the inner smaller-bore devices are removed without requiring withdrawal of the arthroscopic port sheath, whereby proper placement of the port sheath is maintained, and arthroscopic access to the joint space is provided.

According to implementations of the invention, an arthroscopic port introduction system includes an elongate hollow introducing needle and an elongate stylet sized and adapted to be disposed within the elongate hollow introducing needle such that a distal end of the elongate stylet and a distal end of the elongate hollow introducing needle together form a single tissue-penetrating tip. The system also includes an elongate hollow enlarging shaft adapted to be disposed over the elongate hollow introducing needle whereby an operative tissue-penetrating length of the elongate hollow introducing needle is exposed beyond a distal end of the elongate hollow enlarging shaft, and wherein the elongate hollow introducing needle can be removed in a proximal direction from the elongate hollow enlarging shaft. The system further includes an arthroscopic port sheath adapted to be disposed over the elongate hollow enlarging shaft whereby an operative tissue-penetrating length of the elongate hollow enlarging shaft is exposed beyond a distal end of the arthroscopic port sheath, and wherein the elongate hollow enlarging shaft can be removed in a proximal direction from the arthroscopic port sheath.

The arthroscopic port introduction system may be adapted to be fully assembled with the operative tissue-penetrating length of the elongate hollow introducing needle protruding distally beyond the distal end of the elongate hollow enlarging shaft and the tissue-penetrating length of the elongate hollow enlarging shaft protruding distally beyond the distal end of the arthroscopic port sheath. The arthroscopic port introduction system may be adapted to have the distal end of the elongate hollow introducing needle inserted into an arthroscopic space such that the elongate hollow introducing needle is inserted into tissue up to a maximum of the operative tissue-penetrating length of the elongate hollow introducing needle. The arthroscopic port introduction system may be adapted to, without withdrawing the elongate hollow introducing needle from the arthroscopic space, have the distal end of the elongate hollow enlarging shaft advanced into the arthroscopic space such that the elongate hollow enlarging shaft is inserted into the tissue up to a maximum of the operative tissue-penetrating length of the elongate hollow enlarging shaft. The arthroscopic port introduction system may be adapted to, without withdrawing the elongate hollow enlarging shaft from the arthroscopic space, have the distal end of the arthroscopic port sheath advanced into the arthroscopic space through tissue along a path occupied by the elongate hollow enlarging shaft. The arthroscopic port introduction system may also be adapted to, without withdrawing the arthroscopic port sheath, withdraw the elongate stylet, the elongate hollow introducing needle, and the elongate hollow enlarging shaft proximally from within the arthroscopic port sheath, thereby creating an open passage through the arthroscopic port sheath from a location exterior to a patient body to the arthroscopic space to permit the passage of an arthroscopic instrument therethrough.

The tissue-penetrating tip may include a beveled tip. The elongate stylet may include a stylet handle adapted to facilitate insertion or withdrawal of the elongate stylet into and from tissue and into and from the elongate hollow introducing needle. The elongate hollow introducing needle may include a needle handle adapted to facilitate insertion or withdrawal of the elongate hollow introducing needle into and from tissue and into and from the elongate hollow enlarging shaft. The elongate hollow enlarging shaft may include an enlarging shaft handle adapted to facilitate insertion or withdrawal of the elongate hollow enlarging shaft into and from tissue and into and from the arthroscopic port sheath. The arthroscopic port sheath may include a structure adapted to serve as a port sheath handle adapted to facilitate insertion or withdrawal of the port sheath into and from tissue and to secure the arthroscopic port sheath during insertion, manipulation, and withdrawal of an arthroscopic instrument during an arthroscopic procedure.

The enlarging shaft handle may include a hole sized to permit passage of the hollow introducing needle therethrough into the elongate hollow enlarging shaft, and the needle handle may include a hole sized to permit passage of the elongate stylet therethrough into the elongate hollow introducing needle. The elongate stylet may have an outer diameter. The elongate hollow introducing needle may have an inner diameter slightly larger than the outer diameter of the elongate stylet, such that the elongate stylet can move within the elongate hollow introducing needle smoothly and easily, but without significant lateral play. The elongate hollow introducing needle may have an outer diameter. The elongate hollow enlarging shaft may have an inner diameter slightly larger than the outer diameter of the elongate hollow introducing needle, such that the elongate hollow introducing needle can move within the elongate hollow enlarging shaft smoothly and easily, but without significant lateral play. The elongate enlarging shaft may have an outer diameter. The arthroscopic port sheath may have an inner diameter slightly larger than the outer diameter of the elongate hollow enlarging shaft, such that the elongate hollow enlarging shaft can move within the arthroscopic port sheath smoothly and easily, but without significant lateral play.

The distal end of the elongate hollow enlarging shaft and the distal end of the arthroscopic port sheath may be provided with a tissue-penetrating shape. The elongate stylet, the elongate hollow introducing needle, the elongate hollow enlarging rod, and the arthroscopic port sheath may be sized for use with a TMJ procedure. The arthroscopic port introduction system may include one or more additional elongate hollow enlarging shafts concentrically disposed about the elongate hollow enlarging shaft and within the arthroscopic port sheath.

Each of the elongate hollow introducing needle, the elongate hollow enlarging shaft, and the arthroscopic port sheath may include a penetration depth marking spaced from the respective distal ends thereof to guide a depth of placement of the elongate hollow introducing needle, of the elongate hollow enlarging shaft, and the arthroscopic port sheath within an arthroscopic space. The penetration depth markings may be part of a series of penetration depth markings visible on a distal exterior surface of each of the elongate hollow introducing needle, the elongate hollow enlarging shaft, and the arthroscopic port sheath.

According to certain implementations of the invention, a method of use of an arthroscopic port introduction system to introduce an arthroscopic port sheath through surrounding tissue to an arthroscopic joint space includes a step of assembling an arthroscopic port introduction system. The arthroscopic port introduction system includes an arthroscopic port sheath having a distal tip, a hollow enlarging shaft disposed within and having a distal tip protruding distally beyond the distal tip of the arthroscopic port sheath at least a desired tissue-penetrating distance, a hollow introducing needle disposed within and protruding distally beyond the distal tip of the hollow enlarging shaft at least a desired tissue-penetrating distance, and a stylet disposed within and extending substantially an entire length of the hollow introducing needle to provide strength and stiffness thereto. The method further includes steps of inserting a distal end of the hollow introducing needle and the stylet simultaneously through surrounding tissue into an arthroscopic joint space and without withdrawing the hollow introducing needle from the arthroscopic joint space, advancing the distal tip of the hollow enlarging shaft through the surrounding tissue into the arthroscopic joint space. The method also includes steps of without withdrawing the hollow enlarging shaft from the arthroscopic joint space, inserting the distal tip of the arthroscopic port sheath into the arthroscopic joint space, and withdrawing the stylet, the hollow introducing needle, and the hollow enlarging shaft proximally from the arthroscopic port sheath.

After the distal end of the hollow introducing needle and the stylet are inserted into the arthroscopic joint space, the method also may include at least partially withdrawing the stylet from the hollow introducing needle to verify placement of the distal end of the hollow introducing needle within the arthroscopic joint space. The step of inserting the distal end of the hollow introducing needle and the stylet may be facilitated by a stylet handle attached to a proximal end of the stylet. The step of advancing the distal tip of the hollow enlarging shaft may be facilitated by an enlarging shaft handle attached to a proximal end of the hollow enlarging shaft. The step of inserting the distal tip of the arthroscopic port sheath may be facilitated by a structure adapted to serve as a port sheath handle.

The steps of inserting the distal end of the hollow introducing needle and the stylet, advancing the distal tip of the hollow enlarging shaft, and inserting the distal tip of the arthroscopic port sheath may be guided by penetration depth markings on distal exterior surfaces of the hollow introducing needle, the hollow enlarging shaft, and the arthroscopic port sheath.

According to some implementations of the invention, a method of use of an arthroscopic port introduction system to introduce an arthroscopic port sheath through surrounding tissue to an arthroscopic joint space includes a step of providing an arthroscopic port introduction system. The arthroscopic port introduction system includes an arthroscopic port sheath having a distal tip, a hollow enlarging shaft disposed within and having a distal tip protruding distally beyond the distal tip of the arthroscopic port sheath at least a desired tissue-penetrating distance, a hollow introducing needle disposed within and protruding distally beyond the distal tip of the hollow enlarging shaft at least a desired tissue-penetrating distance, and a stylet disposed within and extending substantially an entire length of the hollow introducing needle to provide strength and stiffness thereto. The method further includes steps of inserting a distal end of the hollow introducing needle and the stylet simultaneously through surrounding tissue into an arthroscopic joint space and without withdrawing the hollow introducing needle from the arthroscopic joint space, advancing the distal tip of the hollow enlarging shaft through the surrounding tissue into the arthroscopic joint space. The method also includes steps of without withdrawing the hollow enlarging shaft from the arthroscopic joint space, inserting the distal tip of the arthroscopic port sheath into the arthroscopic joint space, and withdrawing the stylet, the hollow introducing needle, and the hollow enlarging shaft proximally from the arthroscopic port sheath.

After the distal end of the hollow introducing needle and the stylet are inserted into the arthroscopic joint space, the method also may include at least partially withdrawing the stylet from the hollow introducing needle to verify placement of the distal end of the hollow introducing needle within the arthroscopic joint space. The step of inserting the distal end of the hollow introducing needle and the stylet may be facilitated by a stylet handle attached to a proximal end of the stylet. The step of advancing the distal tip of the hollow enlarging shaft may be facilitated by an enlarging shaft handle attached to a proximal end of the hollow enlarging shaft. The step of inserting the distal tip of the arthroscopic port sheath may be facilitated by a structure adapted to serve as a port sheath handle.

The steps of inserting the distal end of the hollow introducing needle and the stylet, advancing the distal tip of the hollow enlarging shaft, and inserting the distal tip of the arthroscopic port sheath may be guided by penetration depth markings on distal exterior surfaces of the hollow introducing needle, the hollow enlarging shaft, and the arthroscopic port sheath.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
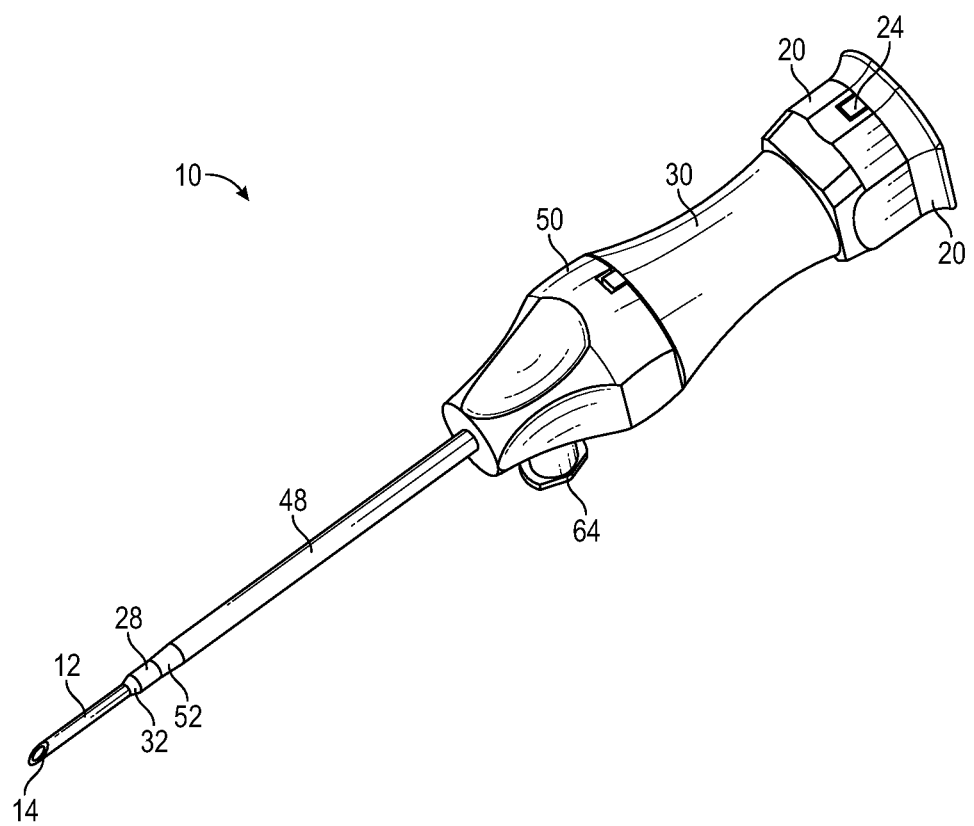
FIG. 1 shows a perspective view of a representative arthroscopic placement assembly in an assembled state.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide devices, systems, and methods for placing and introducing an arthroscopic port into an arthroscopic space, such as within a joint space. By way of example, a joint space that may be accessed using embodiments of the invention may be a temporomandibular joint (TMJ) space, such as, for example, the superior compartment or the inferior compartment, and more specifically, for example, the posterior recess of the superior compartment of the TMJ or the anterior recess of the superior compartment of the TMJ. Embodiments of the invention greatly facilitate proper placement of an access port or arthroscopic port sheath that permits arthroscopic instruments such as cameras, surgical tools, and the like to access the joint space and be used in performing arthroscopic surgical procedures and the like.

While there can be great difficulty in properly placing relatively large-bore access ports in the correct joint space in arthroscopic procedures using traditional methods and systems, even after exploratory placement of smaller-bore needles and the like, embodiments of the invention greatly facilitate proper placement and addresses the difficulty. Embodiments of the invention allow initial proper placement of a relatively small-bore inner needle, followed by advancement of progressively larger-bore devices while the smaller-bore parts of the system remain in place, guaranteeing proper placement of the larger-bore devices. Once the arthroscopic port sheath is properly placed, the inner smaller-bore devices are removed without requiring withdrawal of the arthroscopic port sheath, whereby proper placement of the port sheath is maintained, and arthroscopic access to the joint space is provided.

According to embodiments of the invention, an arthroscopic port introduction system includes an elongate hollow introducing needle and an elongate stylet sized and adapted to be disposed within the elongate hollow introducing needle such that a distal end of the elongate stylet and a distal end of the elongate hollow introducing needle together form a single tissue-penetrating tip. The system also includes an elongate hollow enlarging shaft adapted to be disposed over the elongate hollow introducing needle whereby an operative tissue-penetrating length of the elongate hollow introducing needle is exposed beyond a distal end of the elongate hollow enlarging shaft, and wherein the elongate hollow introducing needle can be removed in a proximal direction from the elongate hollow enlarging shaft. The system further includes an arthroscopic port sheath adapted to be disposed over the elongate hollow enlarging shaft whereby an operative tissue-penetrating length of the elongate hollow enlarging shaft is exposed beyond a distal end of the arthroscopic port sheath, and wherein the elongate hollow enlarging shaft can be removed in a proximal direction from the arthroscopic port sheath.

The arthroscopic port introduction system may be adapted to be fully assembled with the operative tissue-penetrating length of the elongate hollow introducing needle protruding distally beyond the distal end of the elongate hollow enlarging shaft and the tissue-penetrating length of the elongate hollow enlarging shaft protruding distally beyond the distal end of the arthroscopic port sheath. The arthroscopic port introduction system may be adapted to have the distal end of the elongate hollow introducing needle inserted into an arthroscopic space such that the elongate hollow introducing needle is inserted into tissue up to a maximum of the operative tissue-penetrating length of the elongate hollow introducing needle. The arthroscopic port introduction system may be adapted to, without withdrawing the elongate hollow introducing needle from the arthroscopic space, have the distal end of the elongate hollow enlarging shaft advanced into the arthroscopic space such that the elongate hollow enlarging shaft is inserted into the tissue up to a maximum of the operative tissue-penetrating length of the elongate hollow enlarging shaft. The arthroscopic port introduction system may be adapted to, without withdrawing the elongate hollow enlarging shaft from the arthroscopic space, have the distal end of the arthroscopic port sheath advanced into the arthroscopic space through tissue along a path occupied by the elongate hollow enlarging shaft. The arthroscopic port introduction system may also be adapted to, without withdrawing the arthroscopic port sheath, withdraw the elongate stylet, the elongate hollow introducing needle, and the elongate hollow enlarging shaft proximally from within the arthroscopic port sheath, thereby creating an open passage through the arthroscopic port sheath from a location exterior to a patient body to the arthroscopic space to permit the passage of an arthroscopic instrument therethrough.

The tissue-penetrating tip may include a beveled tip. The elongate stylet may include a stylet handle adapted to facilitate insertion or withdrawal of the elongate stylet into and from tissue and into and from the elongate hollow introducing needle. The elongate hollow introducing needle may include a needle handle adapted to facilitate insertion or withdrawal of the elongate hollow introducing needle into and from tissue and into and from the elongate hollow enlarging shaft. The elongate hollow enlarging shaft may include an enlarging shaft handle adapted to facilitate insertion or withdrawal of the elongate hollow enlarging shaft into and from tissue and into and from the arthroscopic port sheath. The arthroscopic port sheath may include a structure adapted to serve as a port sheath handle adapted to facilitate insertion or withdrawal of the port sheath into and from tissue and to secure the arthroscopic port sheath during insertion, manipulation, and withdrawal of an arthroscopic instrument during an arthroscopic procedure.

The enlarging shaft handle may include a hole sized to permit passage of the hollow introducing needle therethrough into the elongate hollow enlarging shaft, and the needle handle may include a hole sized to permit passage of the elongate stylet therethrough into the elongate hollow introducing needle. The elongate stylet may have an outer diameter. The elongate hollow introducing needle may have an inner diameter slightly larger than the outer diameter of the elongate stylet, such that the elongate stylet can move within the elongate hollow introducing needle smoothly and easily, but without significant lateral play. The elongate hollow introducing needle may have an outer diameter. The elongate hollow enlarging shaft may have an inner diameter slightly larger than the outer diameter of the elongate hollow introducing needle, such that the elongate hollow introducing needle can move within the elongate hollow enlarging shaft smoothly and easily, but without significant lateral play. The elongate enlarging shaft may have an outer diameter. The arthroscopic port sheath may have an inner diameter slightly larger than the outer diameter of the elongate hollow enlarging shaft, such that the elongate hollow enlarging shaft can move within the arthroscopic port sheath smoothly and easily, but without significant lateral play.

The distal end of the elongate hollow enlarging shaft and the distal end of the arthroscopic port sheath may be provided with a tissue-penetrating shape. The elongate stylet, the elongate hollow introducing needle, the elongate hollow enlarging rod, and the arthroscopic port sheath may be sized for use with a TMJ procedure. The arthroscopic port introduction system may include one or more additional elongate hollow enlarging shafts concentrically disposed about the elongate hollow enlarging shaft and within the arthroscopic port sheath.

Each of the elongate hollow introducing needle, the elongate hollow enlarging shaft, and the arthroscopic port sheath may include a penetration depth marking spaced from the respective distal ends thereof to guide a depth of placement of the elongate hollow introducing needle, of the elongate hollow enlarging shaft, of the arthroscopic port sheath within an arthroscopic space. The penetration depth markings may be part of a series of penetration depth markings visible on a distal exterior surface of each of the elongate hollow introducing needle, the elongate hollow enlarging shaft, and the arthroscopic port sheath.

According to certain embodiments of the invention, a method of use of an arthroscopic port introduction system to introduce an arthroscopic port sheath through surrounding tissue to an arthroscopic joint space includes a step of assembling an arthroscopic port introduction system. The arthroscopic port introduction system includes an arthroscopic port sheath having a distal tip, a hollow enlarging shaft disposed within and having a distal tip protruding distally beyond the distal tip of the arthroscopic port sheath at least a desired tissue-penetrating distance, a hollow introducing needle disposed within and protruding distally beyond the distal tip of the hollow enlarging shaft at least a desired tissue-penetrating distance, and a stylet disposed within and extending substantially an entire length of the hollow introducing needle to provide strength and stiffness thereto. The method further includes steps of inserting a distal end of the hollow introducing needle and the stylet simultaneously through surrounding tissue into an arthroscopic joint space and without withdrawing the hollow introducing needle from the arthroscopic joint space, advancing the distal tip of the hollow enlarging shaft through the surrounding tissue into the arthroscopic joint space. The method also includes steps of without withdrawing the hollow enlarging shaft from the arthroscopic joint space, inserting the distal tip of the arthroscopic port sheath into the arthroscopic joint space, and withdrawing the stylet, the hollow introducing needle, and the hollow enlarging shaft proximally from the arthroscopic port sheath.

After the distal end of the hollow introducing needle and the stylet are inserted into the arthroscopic joint space, the method also may include at least partially withdrawing the stylet from the hollow introducing needle to verify placement of the distal end of the hollow introducing needle within the arthroscopic joint space. The step of inserting the distal end of the hollow introducing needle and the stylet may be facilitated by a stylet handle attached to a proximal end of the stylet. The step of advancing the distal tip of the hollow enlarging shaft may be facilitated by an enlarging shaft handle attached to a proximal end of the hollow enlarging shaft. The step of inserting the distal tip of the arthroscopic port sheath may be facilitated by a structure adapted to serve as a port sheath handle.

The steps of inserting the distal end of the hollow introducing needle and the stylet, advancing the distal tip of the hollow enlarging shaft, and inserting the distal tip of the arthroscopic port sheath may be guided by penetration depth markings on distal exterior surfaces of the hollow introducing needle, the hollow enlarging shaft, and the arthroscopic port sheath.

According to some embodiments of the invention, a method of use of an arthroscopic port introduction system to introduce an arthroscopic port sheath through surrounding tissue to an arthroscopic joint space includes a step of providing an arthroscopic port introduction system. The arthroscopic port introduction system includes an arthroscopic port sheath having a distal tip, a hollow enlarging shaft disposed within and having a distal tip protruding distally beyond the distal tip of the arthroscopic port sheath at least a desired tissue-penetrating distance, a hollow introducing needle disposed within and protruding distally beyond the distal tip of the hollow enlarging shaft at least a desired tissue-penetrating distance, and a stylet disposed within and extending substantially an entire length of the hollow introducing needle to provide strength and stiffness thereto. The method further includes steps of inserting a distal end of the hollow introducing needle and the stylet simultaneously through surrounding tissue into an arthroscopic joint space and without withdrawing the hollow introducing needle from the arthroscopic joint space, advancing the distal tip of the hollow enlarging shaft through the surrounding tissue into the arthroscopic joint space. The method also includes steps of without withdrawing the hollow enlarging shaft from the arthroscopic joint space, inserting the distal tip of the arthroscopic port sheath into the arthroscopic joint space, and withdrawing the stylet, the hollow introducing needle, and the hollow enlarging shaft proximally from the arthroscopic port sheath.

After the distal end of the hollow introducing needle and the stylet are inserted into the arthroscopic joint space, the method also may include at least partially withdrawing the stylet from the hollow introducing needle to verify placement of the distal end of the hollow introducing needle within the arthroscopic joint space. The step of inserting the distal end of the hollow introducing needle and the stylet may be facilitated by a stylet handle attached to a proximal end of the stylet. The step of advancing the distal tip of the hollow enlarging shaft may be facilitated by an enlarging shaft handle attached to a proximal end of the hollow enlarging shaft. The step of inserting the distal tip of the arthroscopic port sheath may be facilitated by a structure adapted to serve as a port sheath handle.

The steps of inserting the distal end of the hollow introducing needle and the stylet, advancing the distal tip of the hollow enlarging shaft, and inserting the distal tip of the arthroscopic port sheath may be guided by penetration depth markings on distal exterior surfaces of the hollow introducing needle, the hollow enlarging shaft, and the arthroscopic port sheath.

Figure 2:
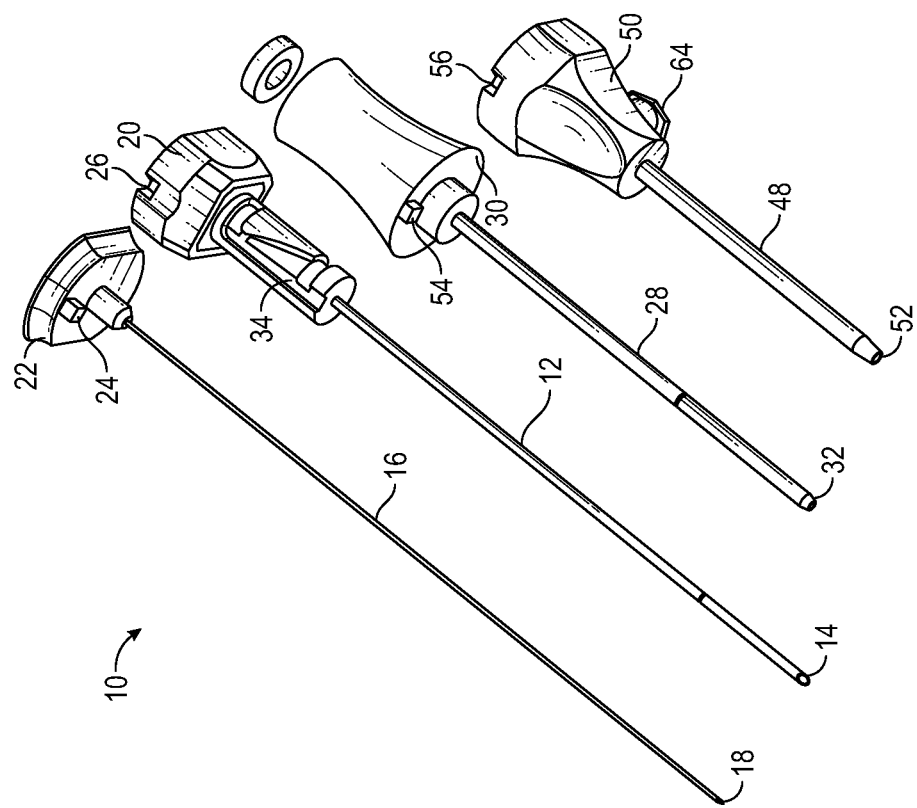
FIG. 2 shows a perspective view of a representative arthroscopic placement assembly in an exploded or disassembled state.
Figure 3:
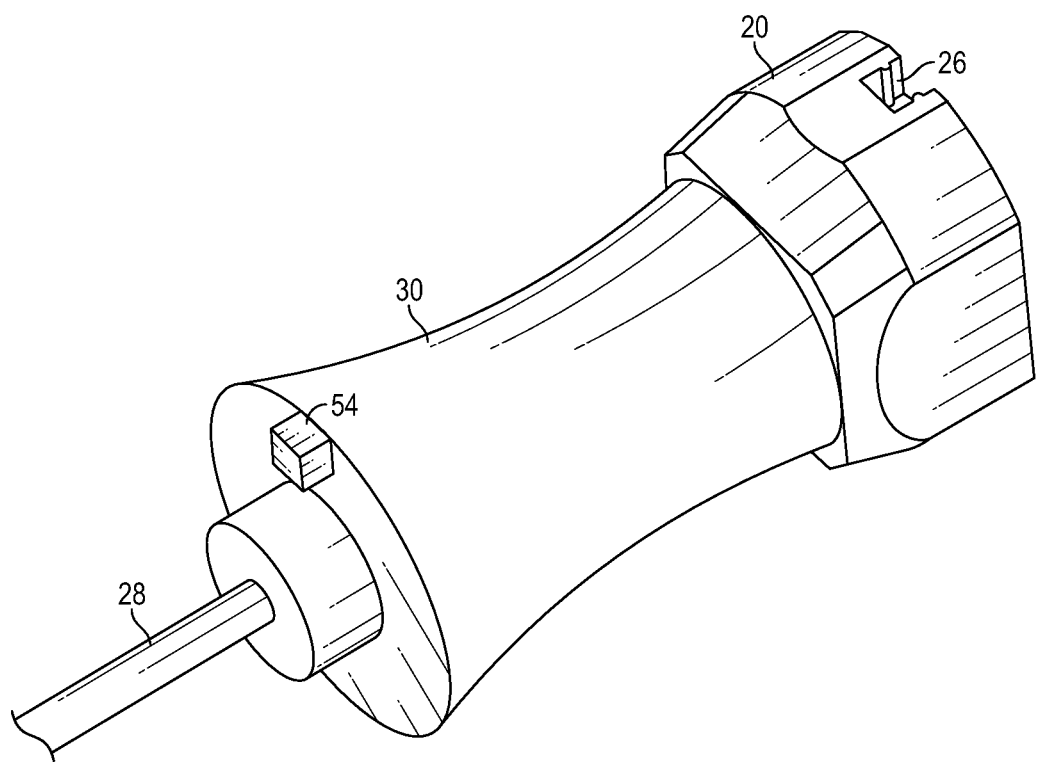
FIG. 3 shows a perspective view of a proximal end of an elongate hollow introducing needle (or introducer) assembled with an elongate hollow enlarging shaft (or dilator)
Figure 4:
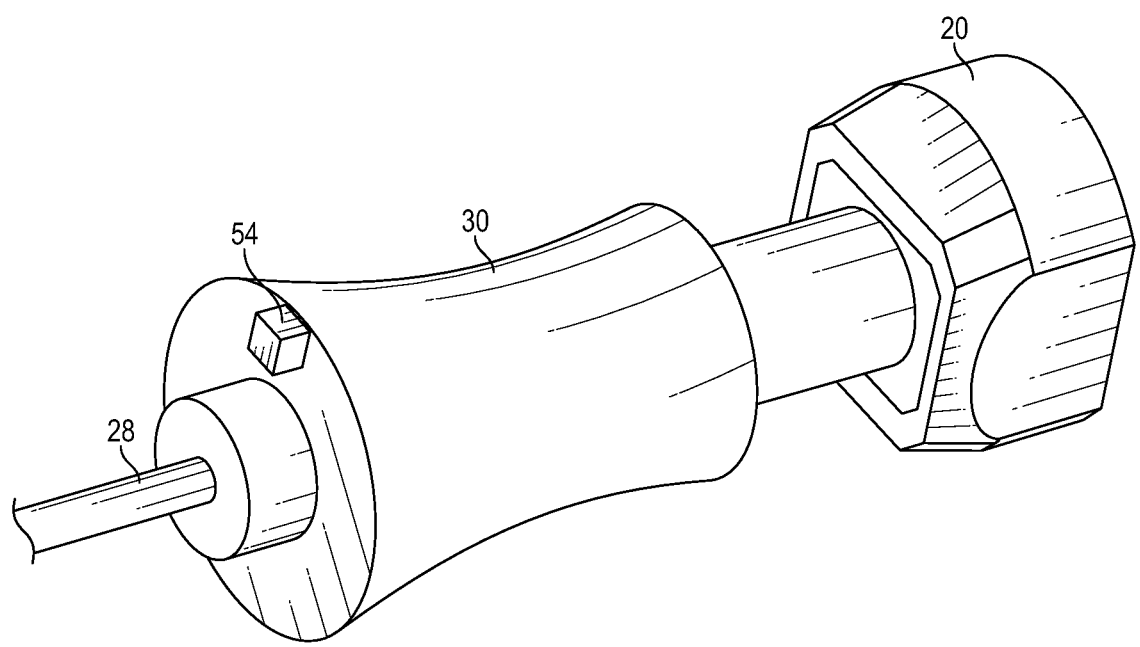
FIG. 4 shows a perspective view of a proximal end of an elongate hollow introducing needle within but partially removed from an elongate hollow enlarging shaft.
Figure 5:
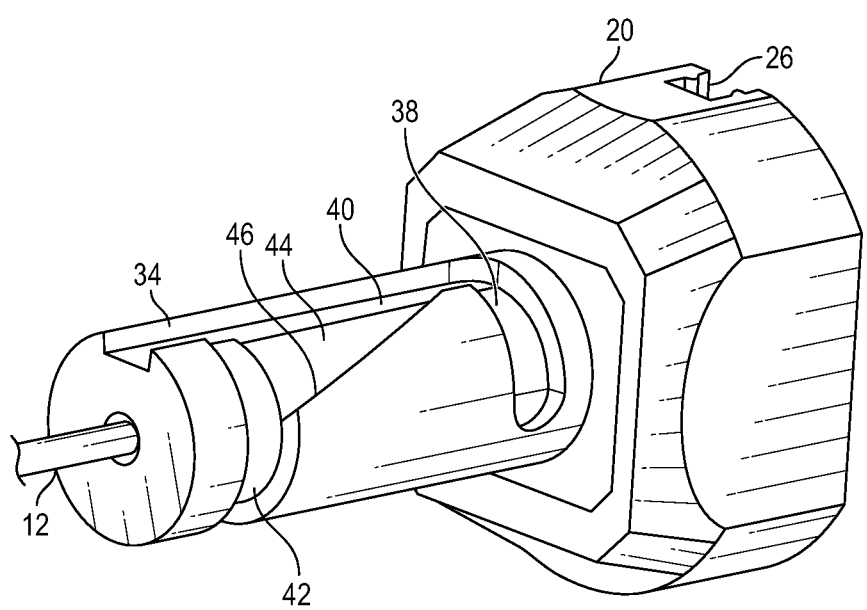
FIG. 5 shows a perspective view of a proximal end of an elongate hollow introducing needle.
Figure 6:
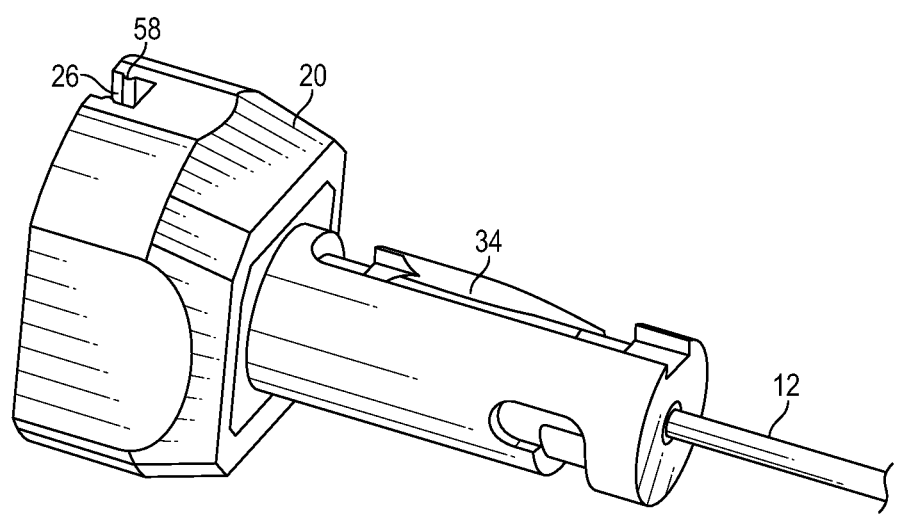
FIG. 6 shows an alternate perspective view of a proximal end of an elongate hollow introducing needle.
Figure 7:
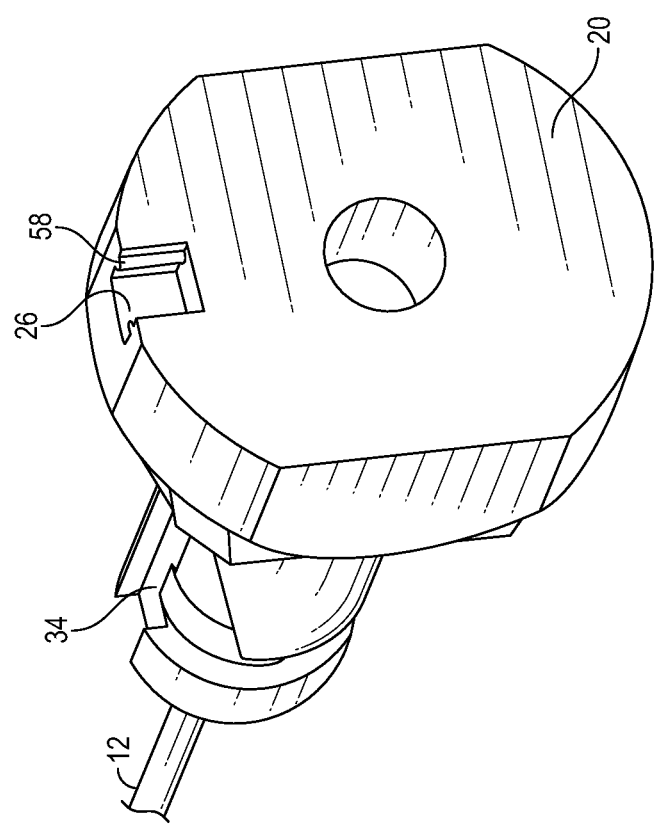
FIG. 7 shows an alternate perspective view of a proximal end of an elongate hollow introducing needle.
Figure 8:
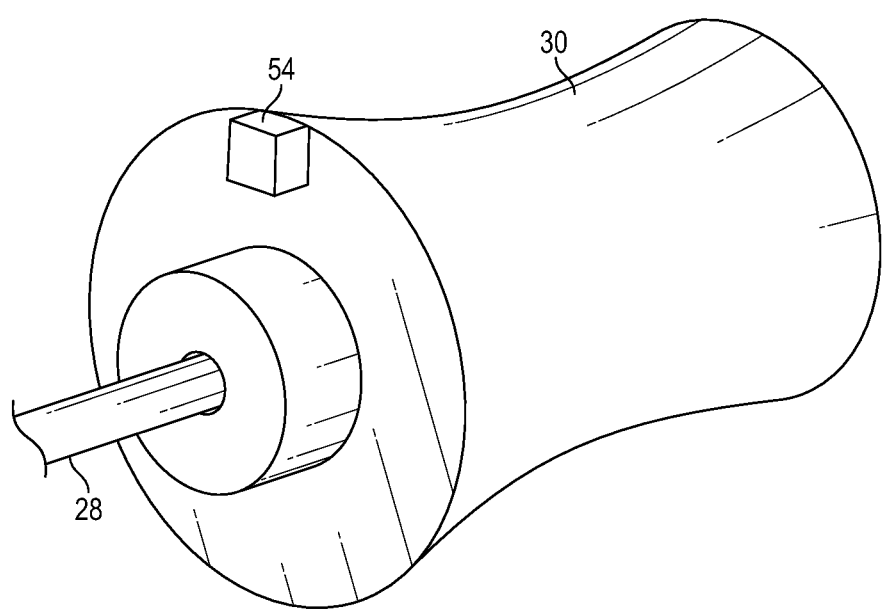
FIG. 8 shows a perspective view of a proximal end of an elongate hollow enlarging shaft.

FIG. 1 shows a perspective view of one embodiment of an arthroscopic placement assembly 10 fully assembled, while FIG. 2 shows a perspective view of the assembly 10 disassembled. The assembly 10 assists in proper placement of an arthroscope into a joint space such as a TMJ space. The assembly 10, when in its assembled state as shown in FIG. 1, is prepared for use to provide access to the joint space. The assembly 10 allows the doctor or other practitioner to initially access the joint space with a narrow-diameter distal tip, wherein the narrower diameter of the distal tip (compared with the diameter of a traditional arthroscopic cannula) is easier to introduce correctly into the tight joint space and also provides improved feel to the doctor as the system 10 is inserted into the joint space. Accordingly, embodiments of the assembly 10 such as that shown in FIG. 1 greatly improve the chances for most favorable outcomes of arthroscopic joint procedures.

Some embodiments of the assembly 10 are provided to the practitioner in an assembled state. Other embodiments of the assembly 10 are provided to the practitioner in a disassembled or partially assembled state. In embodiments where the assembly 10 is not fully assembled, the practitioner fully assembles the assembly 10 before using the assembly 10 in the arthroscopic procedure.

Figure 10:
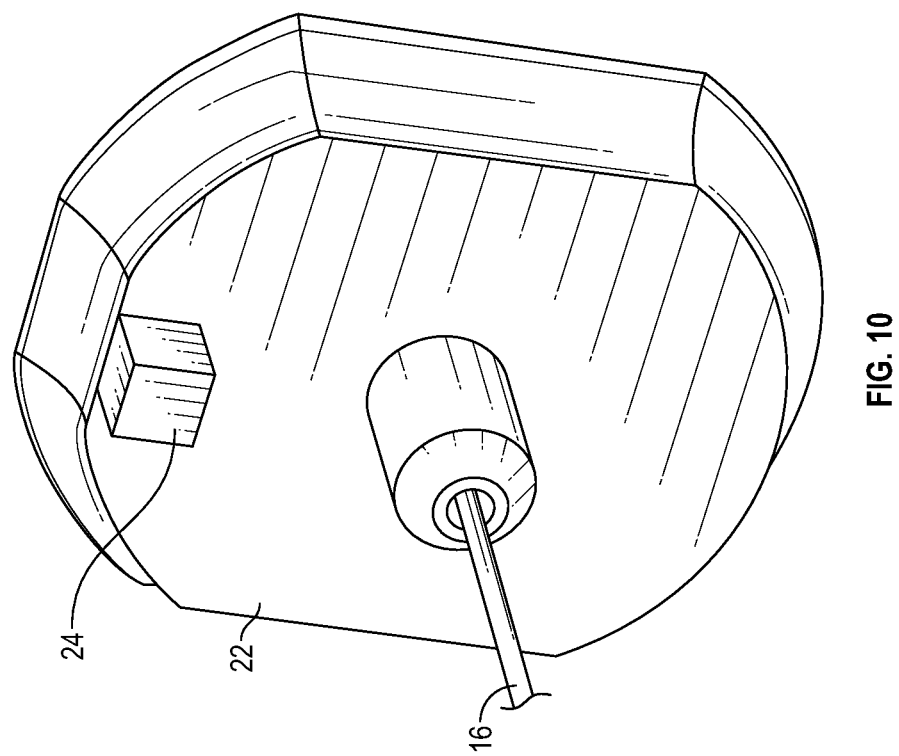
FIG. 10 shows a perspective view of a proximal end of an elongate stylet (or irrigation needle)
Figure 11:
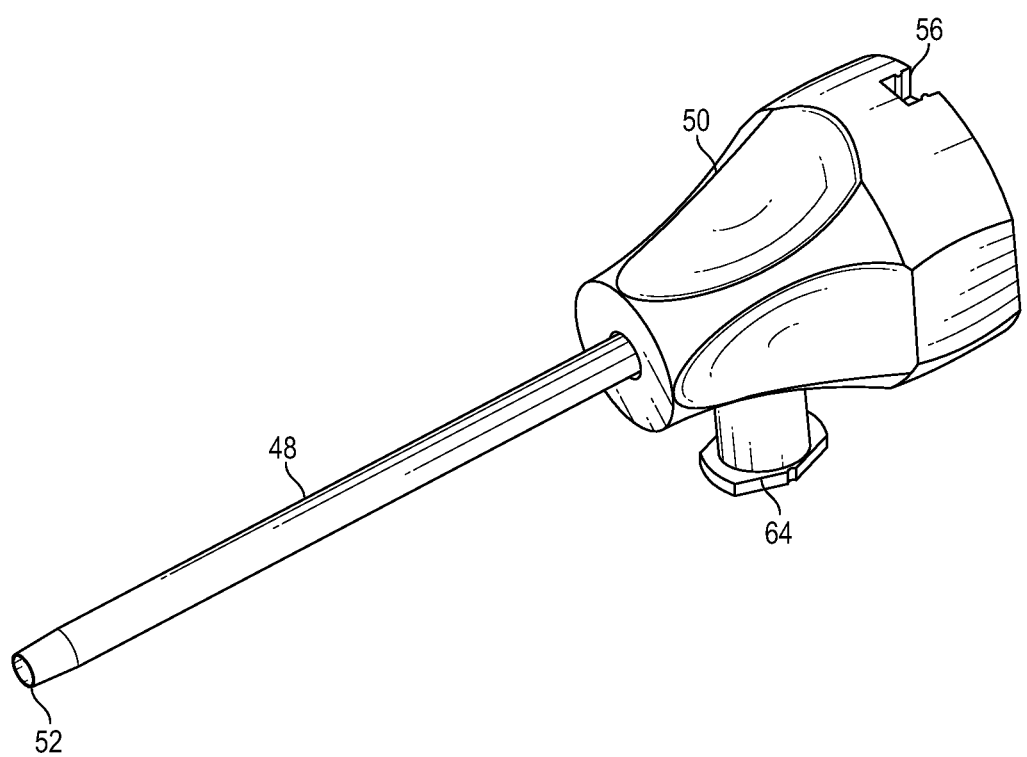
FIG. 11 shows a perspective view of an arthroscopic port sheath (or cannula)
Figure 12:
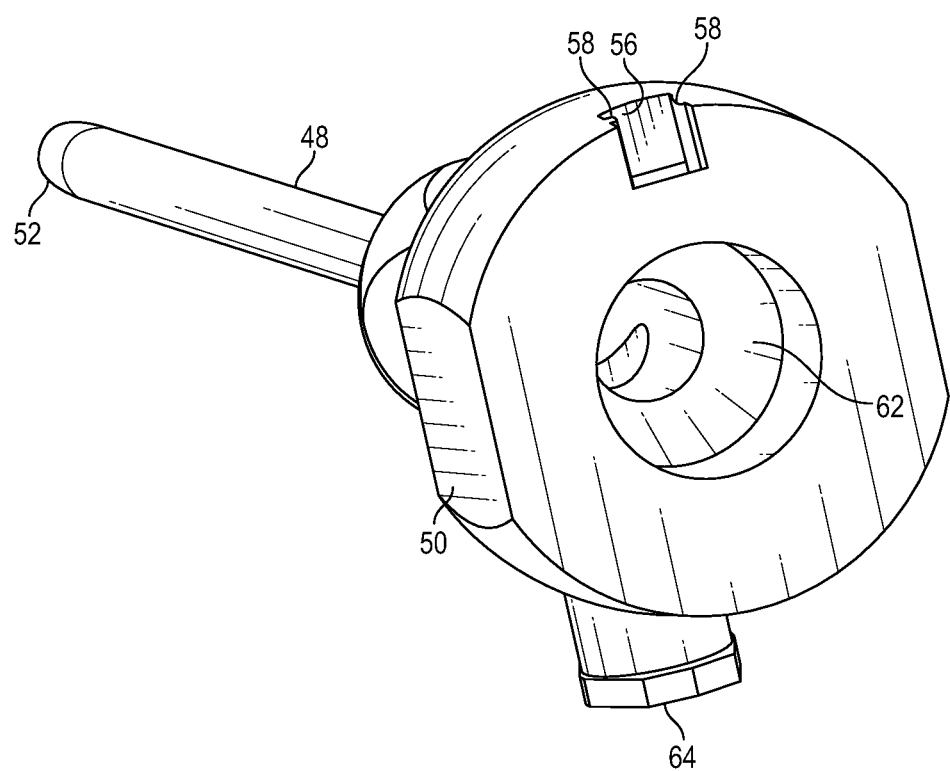
FIG. 12 shows an alternate perspective view of an arthroscopic port sheath.

The assembly 10 includes an elongate hollow introducing needle 12 or inserter (see FIGS. 3-7. The introducing needle 12 has an outer diameter that is comparatively narrow when compared with the other hollow elements of the assembly, allowing the introducing needle 12 to be used for initial penetration of the assembly into the joint space of interest, achieving the benefits of improved feel and ease of introduction already discussed. The introducing needle 12 includes a beveled distal tip 14 in the illustrated embodiment. In other embodiments, the distal tip 14 is not beveled. In the assembled configuration of the illustrated embodiment, an elongate stylet 16 (see FIGS. 2 and 10) is disposed within the introducing needle 12 and has a distal tip 18 that is also beveled in this embodiment and that extends such that the beveled distal tip 18 of the stylet 16 extends along the bevel of the introducing needle's distal tip 14. In embodiments where the introducing needle 12 is not beveled at its distal tip 14, the distal tip 18 of the stylet 16 may extend (slightly) beyond the distal tip 14 of the introducing needle 12 to allow the sharpened distal tip 18 of the stylet 16 to make initial penetration into the body of the patient.

The introducing needle 12 also includes a needle handle 20 at its proximal end that is adapted to allow the practitioner to manipulate the introducing needle 12 and to apply force to the introducing needle 12. The practitioner may apply force to the introducing needle 12 through the needle handle 20 as part of the assembled assembly 10 or individually, as desired, as will be described in more detail shortly. Similarly, the stylet 16 includes a stylet handle 22 at its proximal end. The stylet handle 22 is also adapted to allow the practitioner to manipulate the stylet 16 and to apply force to the stylet 16, either individually or as part of the assembly 10.

The needle handle 20 and the stylet handle 22 of the illustrated embodiment are illustrated as having a particular shape. It should be understood that the shapes of the needle handle 20 and the stylet handle 22 are intended to be illustrative only and are not intended to convey that any particular shape of the needle handle 20 and/or stylet handle 22 is desired or required. That said, the needle handle 20 and the stylet handle 22 of the illustrated embodiment have complimentary shapes to allow the introducing needle 12 and the stylet 16 to engagingly mate together in a way that facilitates joint manipulation of the stylet 16 and the introducing needle 12 at the same time. Accordingly, in the illustrated embodiment, the stylet handle 22 includes a stylet nub 24 and the needle handle 20 includes a stylet recess 26 adapted to receive the stylet nub 24. The stylet nub 24 and the stylet recess 26 allow for both visual and tactile confirmation when the stylet 16 is fully inserted into the introducing needle 12 (and the distal tip 18 is appropriately positioned with respect to the distal tip 14 for introduction).

While FIGS. 1-3, 5-7, and 10 illustrate one example of structure to permit visual and tactile confirmation of when the stylet 16 is fully inserted into the introducing needle 12, such example or embodiment is merely illustrative. The stylet nub 24 and the stylet recess 26 shown may be replaced by any structure or combination of elements that permits visual and/or tactile confirmation of full insertion of and placement (e.g., rotation) of the stylet 16 relative to the introducing needle 12. Such structure and/or elements include complementary magnets in some embodiments. In other embodiments, such confirmation is provided solely visually or by a complementary external shape without a direct-engagement physical structure of the type shown in FIGS. 1-3, 5-7 and 10.

As illustrated in FIG. 1, when the stylet 16 is fully inserted into the introducing needle 12, they both extend distally a similar extent and form a joint introducing structure adapted for initial insertion into the joint space. This joint introducing structure extends beyond any other structure of the assembly 10 having a greater diameter. The amount by which this joint introducing structure extends beyond any other structure may vary between embodiments. In some embodiments, the amount by which the joint structure extends corresponds generally to one of an anticipated insertion depth or a maximum safe insertion depth. Accordingly, in such embodiments, the practitioner can use the visual cues of the structure of the assembly 10, upon inserting the distal end of the assembly 10 into the patient and as the assembly 10 is inserted as a guide to penetration depth. In other embodiments, the external surface of the introducing needle 12 is marked with depth markings to assist the practitioner to gauge the depth of penetration and whether the joint space is likely to have been accessed as desired.

When the doctor or other practitioner believes the joint space has been properly accessed (e.g., the distal tips 14, 18 are believed to be within the desired joint space), the doctor can use the stylet handle 22 to withdraw the stylet 16 from within the introducing needle 12 (compare, e.g., FIG. 1 to FIG. 3) to determine whether synovial fluid is present at the distal tip 14. If the fluid is not present, the stylet 16 can be re-inserted and placement adjusted as necessary. If fluid is present, the doctor or other practitioner knows that placement is generally correct and can proceed to further steps of the insertion procedure.

Accordingly, the assembly 10 further includes an elongate hollow enlarging shaft 28 or dilator (see FIGS. 1-4, 8, and 9). The enlarging shaft 28 is adapted to enlarge the access to the joint space by being advanced through the tissue around the introducing needle 12 while the introducing needle 12 remains stationary or relatively stationary with the distal tip 14 in the joint space. Such advancement dilates or enlarges the passage accessing the joint space. Accordingly, the enlarging shaft 28 includes a shaft handle 30 at the proximal end of the enlarging shaft 28 that is adapted to permit the doctor or other practitioner to manipulate the enlarging shaft 28 either independently or as part of the assembly 10. The enlarging shaft 28 also includes a distal tip 32 that is tapered to ease advancement of the enlarging shaft 28 through the tissue into the joint space.

In some embodiments, when the assembly 10 is fully assembled, the distal tip 32 extends a significant amount beyond the distal-most portion of any larger-diameter structures of the assembly 10 to allow the doctor or other practitioner to visualize how far the enlarging shaft 28 has been advanced into the patient's tissue. In some such embodiments, the outer surface of the enlarging shaft is provided with depth markings to permit the practitioner to visualize the depth of insertion of the enlarging shaft 28. In other embodiments, such as that illustrated in FIGS. 1-12, a needle mating structure 34 (see FIGS. 2 and 5-7) on a distal outer surface of the needle handle 20 is formed to engage with a corresponding shaft mating structure 36 (see FIG. 9) on a proximal inner surface of the shaft handle 30.

In use, the needle mating structure 34 and the shaft mating structure 36 engage in a way that facilitates the practitioner's insertion of the enlarging shaft 28 to a desired depth. In practice, the desired depth is the then-current depth of the distal tip 14 of the introducing needle 12. Accordingly, the shaft mating structure 36 is formed as a protruding cylinder or nub extending radially inward from the proximal inner surface of the shaft handle 30. Meanwhile, the needle mating structure 34 includes a proximal circumferential channel 38, a longitudinal channel 40 extending distally from the proximal circumferential channel 38 to the end of the shaft handle 30, and a distal circumferential channel 42 extending from the longitudinal channel 40 near the distal end of the shaft handle 30. A sloped longitudinal enlargement 44 extends along the longitudinal channel, broadening toward the distal end of the shaft handle 30, such that effectively the longitudinal channel 40 is narrow toward the proximal end and wide toward the distal end of the shaft handle 30.

This configuration of the shaft mating structure 34 allows the practitioner to precisely advance the enlarging shaft 28 to the precise depth of the distal tip 14 of the introducing needle 12. When the assembly 10 is fully assembled, the introducing needle 12 is fully inserted into the enlarging shaft 28, with the needle mating structure 34 within the shaft mating structure 36. The introducing needle 12 is rotated clockwise relative to the enlarging shaft 28 (looking down the axis of the assembly 10 from the proximal to the distal end) such that the shaft mating structure 36 is at the end of the proximal circumferential channel away from the longitudinal channel 40. In this position, the enlarging shaft 28 cannot inadvertently be moved distally relative to the introducing needle 12.

Once the introducing needle 12 is at the desired depth, the doctor or other practitioner rotates the enlarging shaft 28 clockwise relative to the introducing needle 12 (looking down the axis of the assembly 10 from the proximal to the distal end) or alternatively rotates the introducing needle 12 counterclockwise relative to the enlarging shaft 28 until the shaft mating structure 36 reaches the longitudinal channel 40. At this point, the practitioner slightly advances the enlarging shaft 28 while keeping the introducing needle in place (with the distal tip 14 properly within the joint space) until the shaft mating structure 36 is past the proximal circumferential channel 38. Once the shaft mating structure 36 is past the proximal circumferential channel 38 (e.g., the enlarging shaft 28 has been slightly advanced a sufficient amount), the practitioner applies a slight counter-clockwise force to the enlarging shaft 28 (or optionally a slight clockwise force to the introducing needle 12) (looking down the axis of the assembly 10 from the proximal to the distal end) as the practitioner further advances the enlarging shaft 28 (while holding the introducing needle 12 steady). Doing so causes the shaft mating structure 36 to advance along a ramped edge 46 of the sloped longitudinal enlargement.

The enlarging shaft 28 is advanced in this way until the shaft mating structure 36 reaches the distal circumferential channel 42, at which point the shaft mating structure 36 will be free to rotate counter-clockwise (looking down the axis of the assembly 10 from the proximal to the distal end) within the distal circumferential channel relative to the introducing needle 12. Accordingly, the practitioner is provided with direct and easy-to-interpret physical feedback that the enlarging shaft 28 has been advance until its distal tip 32 has penetrated to the depth of the distal tip 14 of the introducing needle 12 and is thus within the joint space (assuming there has been little to no relative movement of the distal tip 14 relative to the joint space during the advancement of the enlarging shaft 28). At this point, the practitioner knows the distal tip 32 is within the joint space, as desired, and rotates the introducing needle 12 counter-clockwise (looking down the axis of the assembly 10 from the proximal to the distal end) relative to the enlarging shaft 28 until the shaft mating structure 36 is again within the longitudinal channel 40, which can be readily felt by touch, and the practitioner then is free to withdraw the introducing needle 12 from the enlarging shaft 28.

At this point the distal tip 32 of the enlarging shaft 28 is within the joint space and the enlarging shaft 28 provides a passage of enlarged diameter (relative to the inner diameter of the introducing needle 12) to the joint space. This passage of enlarged diameter has been achieved with initial access being achieved with a relatively narrow initial introducing element that is not withdrawn until the enlarging shaft 28 is in place. Accordingly, the passage of enlarged diameter is achieved with the touch and precision provided by the relatively narrow introducing needle 12 without requiring a series of steps of insertion and withdrawal of successively larger-diameter structures.

As may be appreciated, the assembly 10 of various embodiments is capable of being provided with a series of increasing-diameter enlarging shafts such that a passage of essentially any desired diameter can be achieved by using more or fewer enlarging shafts similar to the enlarging shaft 28. As desired, each handle of each successive shaft may be provided with mating structures to facilitate achieving a desired insertion depth, or external markings may be provided at distal ends of each successive shaft to provide visualization of insertion depth of each shaft.

Nevertheless, in the embodiment of the assembly illustrated in FIGS. 1-12, there is only the single enlarging shaft 28. When the assembly 10 is fully assembled, the enlarging shaft 28 is nested within an arthroscopic port sheath 48 or cannula, as illustrated in FIG. 1, with additional views of the arthroscopic port sheath 48 shown in FIGS. 2 and 11-12. In some ways, the arthroscopic port sheath 48 acts as a further enlarger or dilator of the passage formed by the introducing needle 12 and enlarged by the enlarging shaft 28. The arthroscopic port sheath 48 includes a sheath handle 50 sized and adapted to permit manipulation of and application of force to the arthroscopic port sheath 48 either as part of the assembly 10 or individually. The arthroscopic port sheath 48 also has a distal tip 52, which is tapered in the illustrated embodiment.

In some embodiments, the arthroscopic port sheath 48 has a length adapted to permit the enlarging shaft 28 to be fully advanced until the distal tip 32 is within the joint space before the distal tip 52 of the arthroscopic port sheath 48 contacts the skin of the patient. In other embodiments, such as the embodiment shown in FIGS. 1-2 and 11-12, the arthroscopic port sheath 48 is longer, relative to the enlarging shaft 28, such that as the enlarging shaft 28 is pushed distally towards the joint space, the distal tip 52 of the arthroscopic port sheath 48 begins pushing through the patient's tissue before the distal tip 32 of the enlarging shaft 28 reaches the joint space. Once the enlarging shaft 28 is sufficiently advanced, such that the distal tip 32 thereof is within the joint space, and after the introducing needle 12 has been removed therefrom, the enlarging shaft 28 is held in place by the practitioner with the distal tip 32 within the joint space.

At this point in the placement procedure, the handle 30 of the enlarging shaft 28 is held in place while the handle 50 of the arthroscopic port sheath 48 is advanced slightly until the distal tip 52 of the arthroscopic port sheath 48 is within the joint space. The doctor or other practitioner can know the arthroscopic port sheath 48 is properly advanced by visual confirmation of the amount of advancement of the handle 50 relative to the handle 30. As may be seen in FIGS. 1-4, 8, and 11-12, the handle 30 includes a shaft nub 54 and the handle 50 includes a sheath recess 56 sized and placed to receive the shaft. In some embodiments, the sheath recess 56 and/or the stylet recess 26 includes one or more ribs 58 that serve to form a tight fit with the shaft nub 54 and/or the stylet nub 24, respectively, such that the respective components will not separate accidentally, but only after application of a minimum amount of release force therebetween. In some embodiments, once the shaft nub 54 is fully outside of the sheath recess 56 such that the arthroscopic port sheath 48 is able to rotate around the enlarging shaft 28, the arthroscopic port sheath 48 has been sufficiently advanced such that the practitioner knows that the distal tip 52 is within the joint space (assuming the enlarging shaft 28 has been held in place).

Accordingly, once the distal tip 52 is in the joint space, the arthroscopic port sheath 48 can be secured in place for the arthroscopic procedure and the enlarging shaft 28 can be removed. Once the enlarging shaft 28 is removed from the arthroscopic port sheath 48, the arthroscopic port sheath 48 acts as a cannula whereby one or more arthroscopic tools (such as an arthroscope, a fiber-optic camera, a grasper, a punch tip, a biter, a knife, a scoop, a light, a hook, a suturing tool, a retriever, a scissor, a cutter, and the like) can be inserted into the joint space and manipulated as desired.

Embodiments of the invention may be of particular use with respect to small joint spaces such as the TMJ joint space. In TMJ procedures, it is common to use two access points to access the joint with different instruments. Placement of the first, blind, access port can be particularly difficult, especially for less-practiced medical professionals. Embodiments of the invention allow the practitioner to use the narrower-diameter introducing needle 12, which provides greater precision and feel or feedback to the practitioner to initially access the joint space. Then, the practitioner can withdraw the stylet 16 to confirm joint space access (by presence of synovial fluid). The practitioner leaves the introducing needle 12 in the joint space while separating the enlarging shaft 28 and the arthroscopic port sheath 58 from the introducing needle 12 and advancing them into the joint space while the introducing needle 12 is held in place. Once the distal tip 32 of the enlarging shaft 28 is within the joint space, the introducing needle 12 is withdrawn. The arthroscopic port sheath 48 is then separated from the enlarging shaft 28 and advanced slightly until the distal tip 52 is within the joint space while the enlarging shaft 28 is held in place. Then the enlarging shaft 28 is removed.

With the first access placement complete, the arthroscopic port sheath 58 can serve as a cannula for introduction of an arthroscopic camera, such that the joint space can be visualized as the second arthroscopic access is placed, either using a similar system or more simply by using a direct introduction of an arthroscopic cannula with a trocar, as is known in the art.

Figure 9:
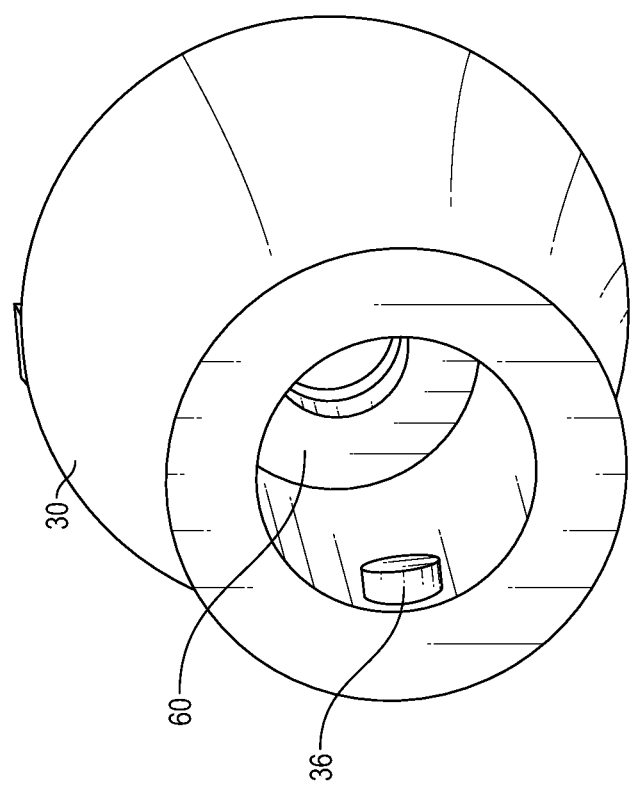
FIG. 9 shows an alternate perspective view of a proximal end of an elongate hollow enlarging shaft.

In some embodiments, as shown in FIGS. 2 and 9, the assembly 10 further includes one or more gaskets 60 or O-rings that provide a watertight seal between elements of the assembly 10 when the assembly 10 is fully assembled. In the embodiment of the assembly 10 illustrated in FIGS. 1-12, the gasket 60 is formed of silicone, and each of the other components includes an elongate member formed of stainless steel or other surgical-grade metal and an a handle formed of a plastic material such as an injection-molded plastic. The exact grade of stainless steel can vary between embodiments, but in some illustrative embodiments the steel parts have a modulus of elasticity of approximately 200 GPa. The exact type of plastic used can also vary between embodiments, but in some embodiments the plastic components are formed of a plastic such as Makrolon 2458 polycarbonate sold by Covestro AG, or the equivalent. As may be appreciated, all components of the assembly 10 are formed of materials that are readily sterilizable. While it is envisioned that the assembly 10 will typically be sold as a pre-sterilized, single-use product, it is possible that some embodiments may be cleaned and sterilized for re-use.

As may be appreciated from FIGS. 1-2 and 11-12, the arthroscopic port sheath 48 includes both a main lumen 62 and a side port 64. In some procedures, the lumen 62 provides passage for the arthroscopic instrument and the side port 64 may be used either for access of another instrument or as a fluid port during the procedure. As may be appreciated, the size and shape of the arthroscopic port sheath 48 shown in FIGS. 1-2 and 11-12 is intended to be illustrative only and not restrictive, and embodiments of the invention embrace the use of arthroscopic port sheaths 48 without the side port 64 or with additional ports and having any desired shape and size of, for example, the sheath handle 50.

Figure 13:
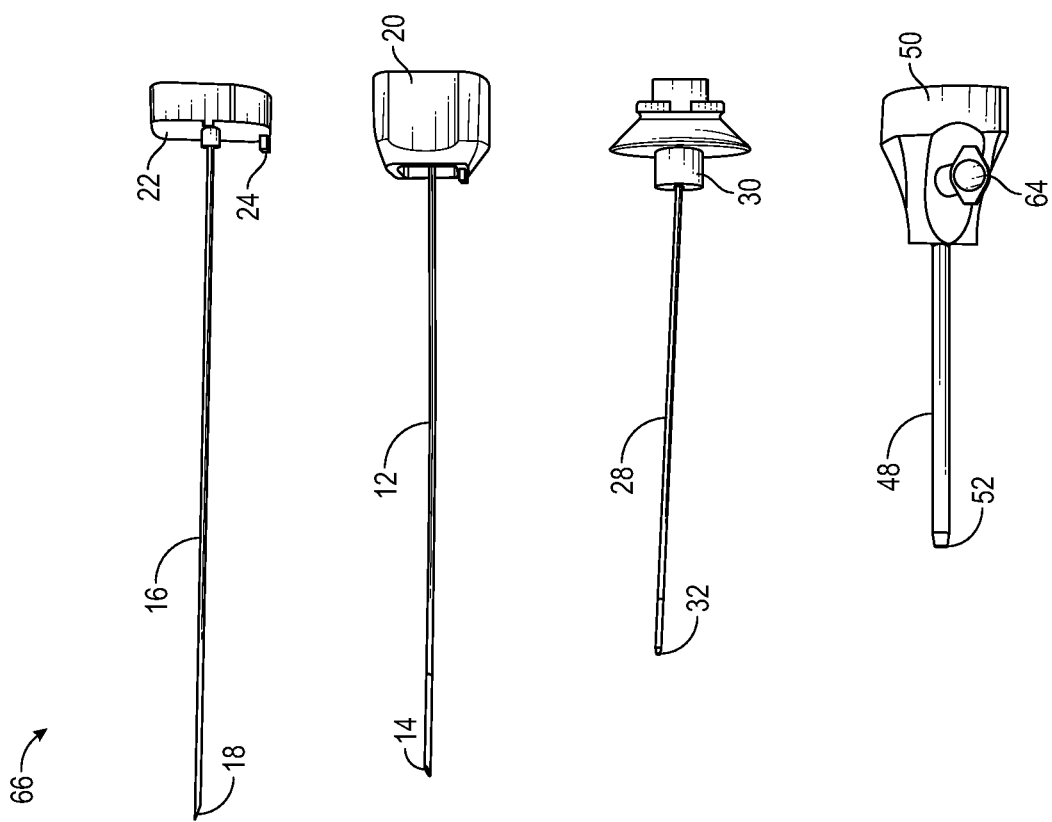
FIG. 13 shows a perspective view of an alternate representative arthroscopic placement assembly in a disassembled state.
Figure 14:
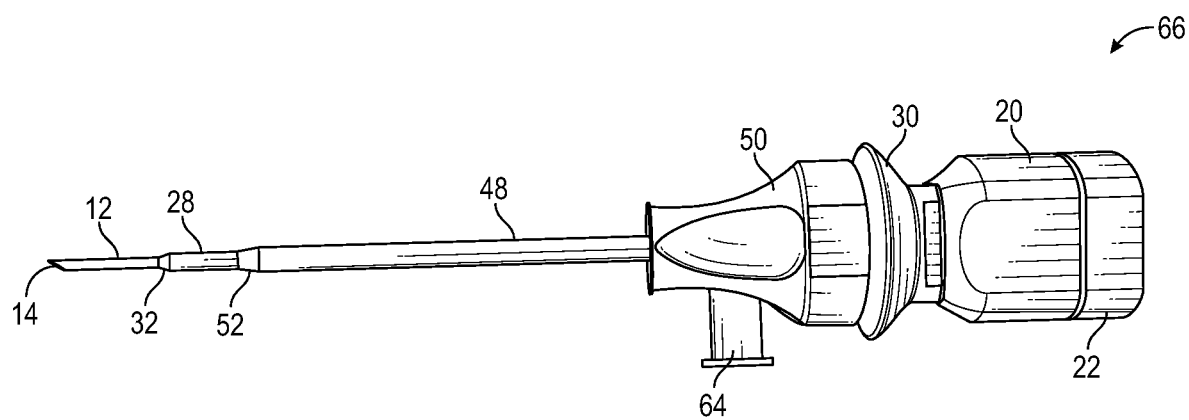
FIG. 14 shows a perspective view of a representative arthroscopic placement assembly in an assembled state.

FIGS. 13 and 14 illustrate an alternate embodiment of an arthroscopic placement assembly 66. This assembly 66 also includes an embodiment of the stylet 16, an embodiment of the introducing needle 12, an embodiment of the enlarging shaft 28, and an embodiment of the arthroscopic port sheath 48. The individual features of these components are in many ways similar to the features discussed with respect to the embodiment of the assembly 10 discussed with respect to FIGS. 1-12. However, the dimensions of the elongate members vary somewhat between the embodiments, and the dimensions and shapes of the various handles 20, 22, 30, and 50 differ between the embodiments. Accordingly, the embodiment of the assembly 66 shown in FIGS. 13 and 14 serves to illustrate one way in which embodiments may vary while still falling within the scope of the disclosed invention. Additionally, the alternate embodiment lacks the tactile advancement and engagement features between the enlarging shaft 28 and the introducing needle 12 (e.g., the needle mating structure 34 and the shaft mating structure 36) discussed with respect to the embodiment of the assembly 10 shown in FIGS. 1-12, instead utilizing visual cues such as depth markings on the elongate member of the enlarging shaft 28 to ensure proper depth of penetration thereof.

Figure 15:
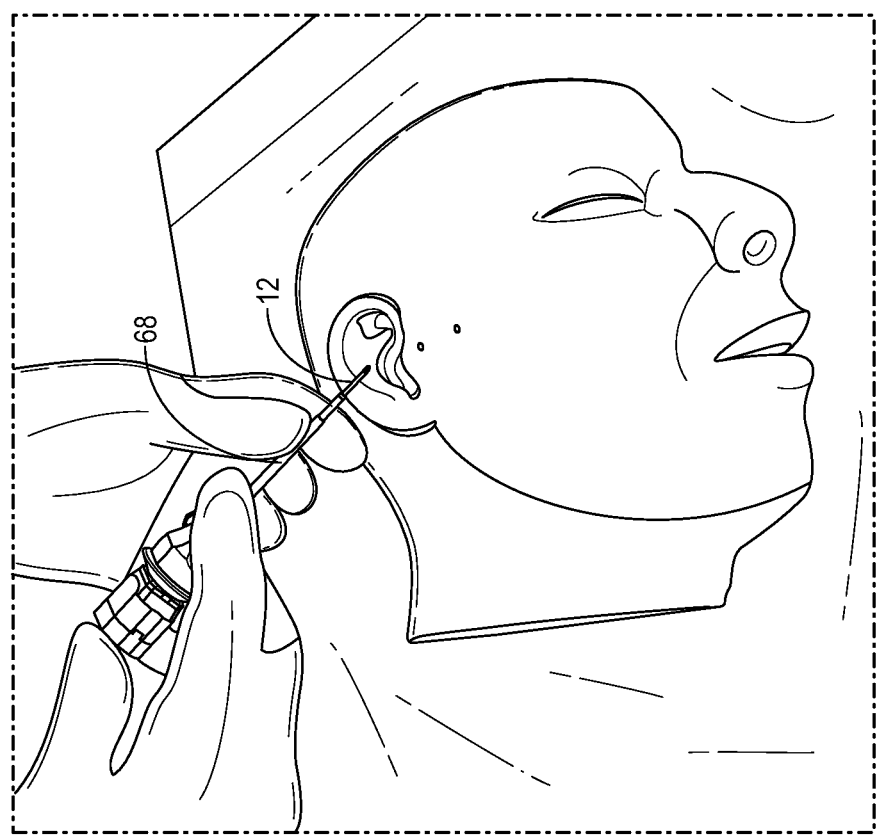
FIG. 15 shows a perspective view of use of a representative arthroscopic placement assembly, wherein the assembled assembly is introduced proximate a patient.
Figure 16:
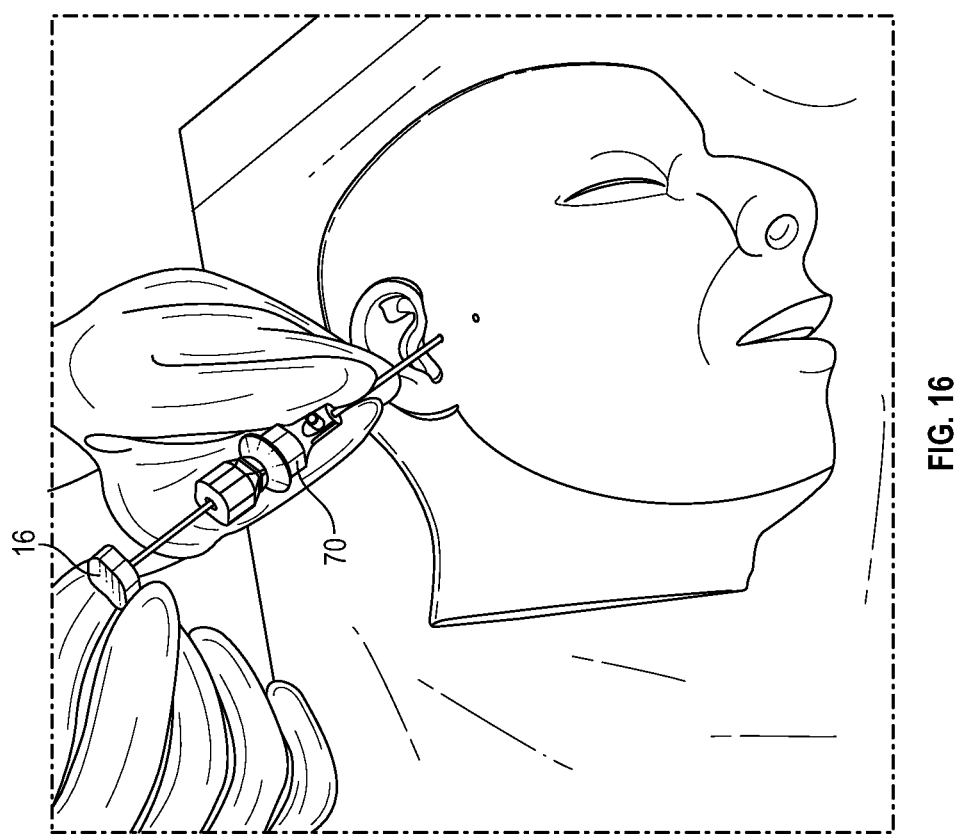
FIG. 16 shows a perspective view of use of the assembly, wherein a distal end of the assembly, primarily a distal tip of an elongate stylus and a distal tip of an elongate hollow introducing needle, has been inserted into the joint space a desired amount, and the elongate stylus is being removed to check for fluid flow.

FIGS. 15-19 illustrate steps for use of an embodiment of an arthroscopic placement assembly such as the assembly 10 or the assembly 66 in an arthroscopic placement procedure into the TMJ joint space as part of a TMJ surgical procedure. As shown in FIG. 15 a fully assembled assembly 68 (representing any embodiment of assembly such as the assembly 10 or the assembly 66 or some other embodiment of an assembly) is brought proximate the patient, and the narrow-diameter distal end of the introducing needle 12 is used to feel along the bone as the distal tip 14 thereof is advanced along the bone and into the joint space. Then, as shown in FIG. 16, the stylet 16 is withdrawn from a first partial assembly 70 (the introducing needle 12, the enlarging shaft 28 and the arthroscopic port sheath 48) to allow the practitioner to check for synovial fluid.

Figure 17:
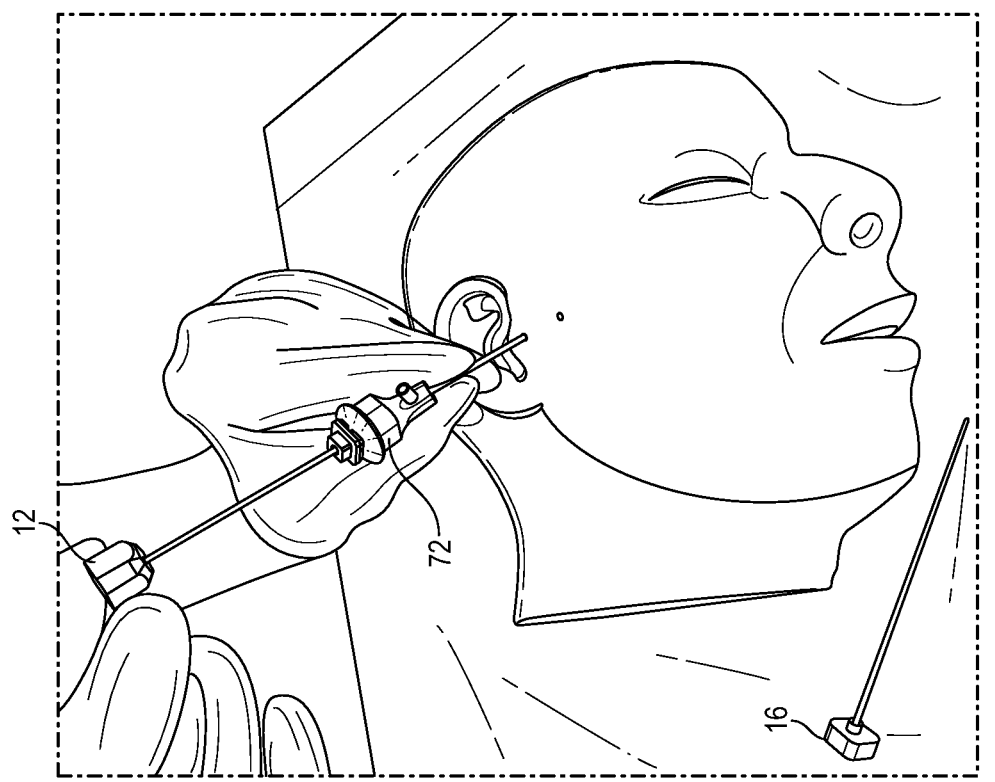
FIG. 17 shows a perspective view of use of the assembly, wherein a distal tip of an elongate hollow enlarging shaft has been advance to the distal tip of the elongate hollow introducing needle within the joint space, and then the elongate hollow introducing needle is being removed from the assembly.

Assuming synovial fluid is present, the stylet 16 is placed aside and the doctor or other practitioner disengages the introducing needle 12 from the remainder of the first partial assembly 70, and advances all but the introducing needle 12 toward the joint space while holding the introducing needle 12 in place. As shown in FIG. 17, once a second partial assembly 72 (the enlarging shaft 28 and the arthroscopic port sheath 48) is advanced until the distal tip 32 of the enlarging shaft is in the joint space, the introducing needle 12 is removed from the second partial assembly 72 and set aside.

Figure 18:
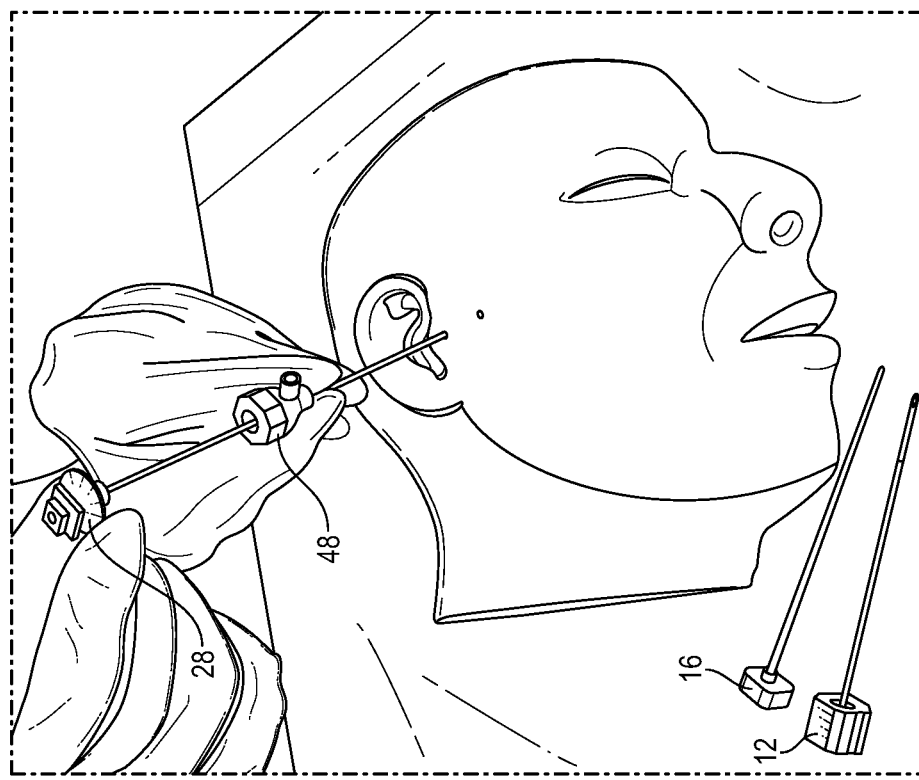
FIG. 18 shows a perspective view of use of the assembly, wherein a distal tip of an arthroscopic port sheath has been advanced to the distal tip of the elongate hollow enlarging shaft within the joint space, and then the elongate hollow enlarging shaft is being removed from the assembly.
Figure 19:
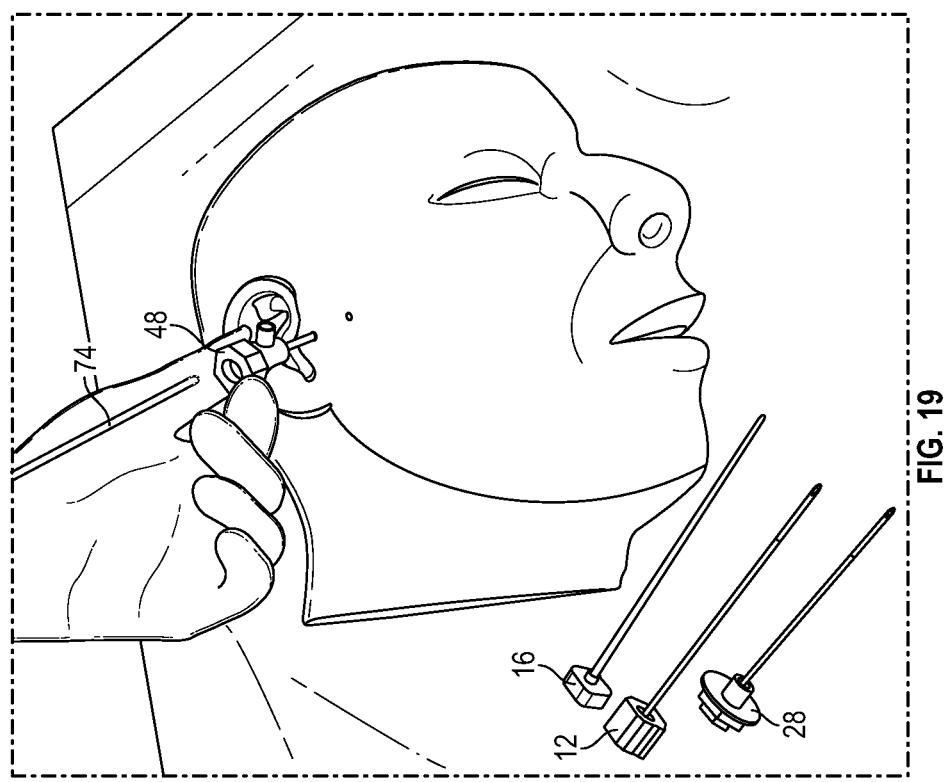
FIG. 19 shows a perspective view of use of the assembly, wherein the elongate hollow enlarging shaft is fully removed from the arthroscopic port sheath with the distal tip of the arthroscopic port sheath is disposed within the joint space such that the arthroscopic port sheath is adapted to serve as a cannula during an arthroscopic procedure.
Figure 20:
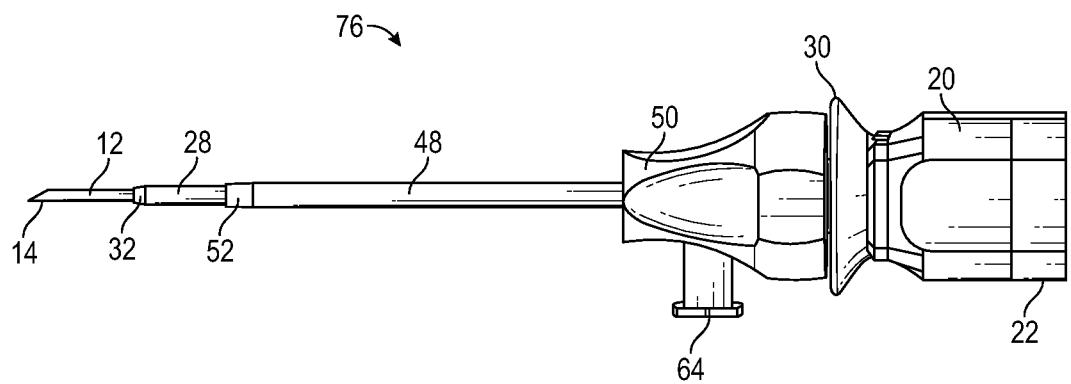
FIG. 20 shows a perspective view of a representative arthroscopic placement assembly in an assembled state.
Figure 21:
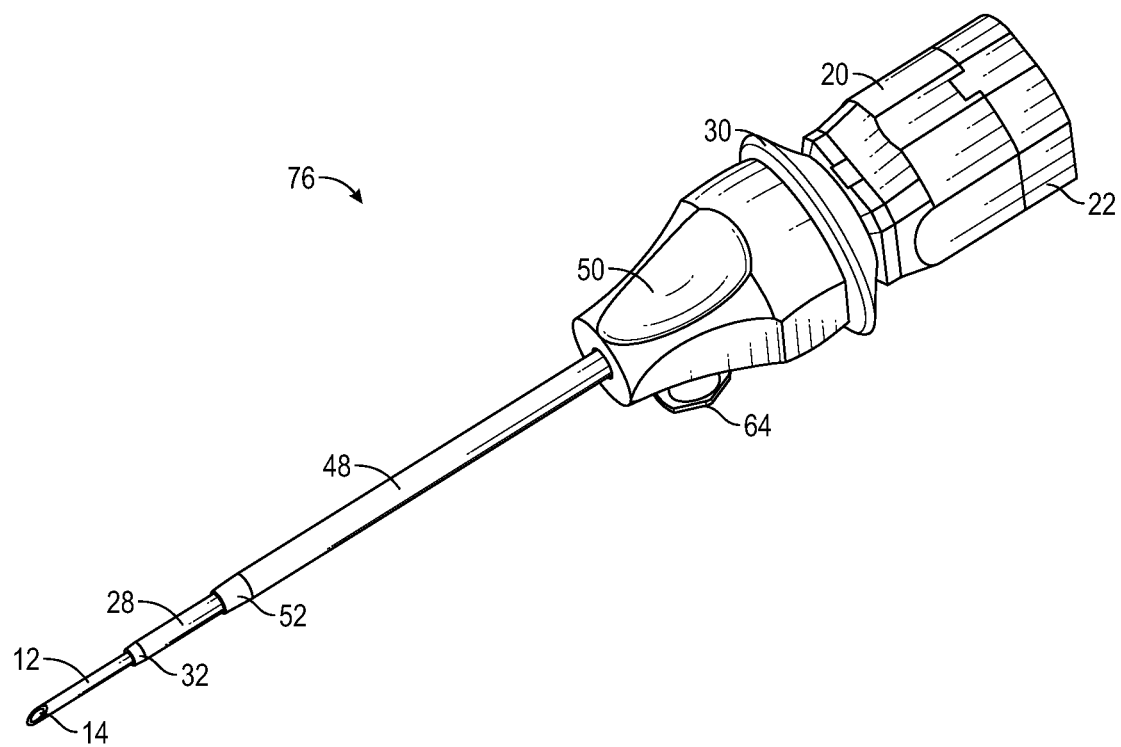
FIG. 21 shows an alternate perspective view of a representative arthroscopic placement assembly in an assembled state.
Figure 22:
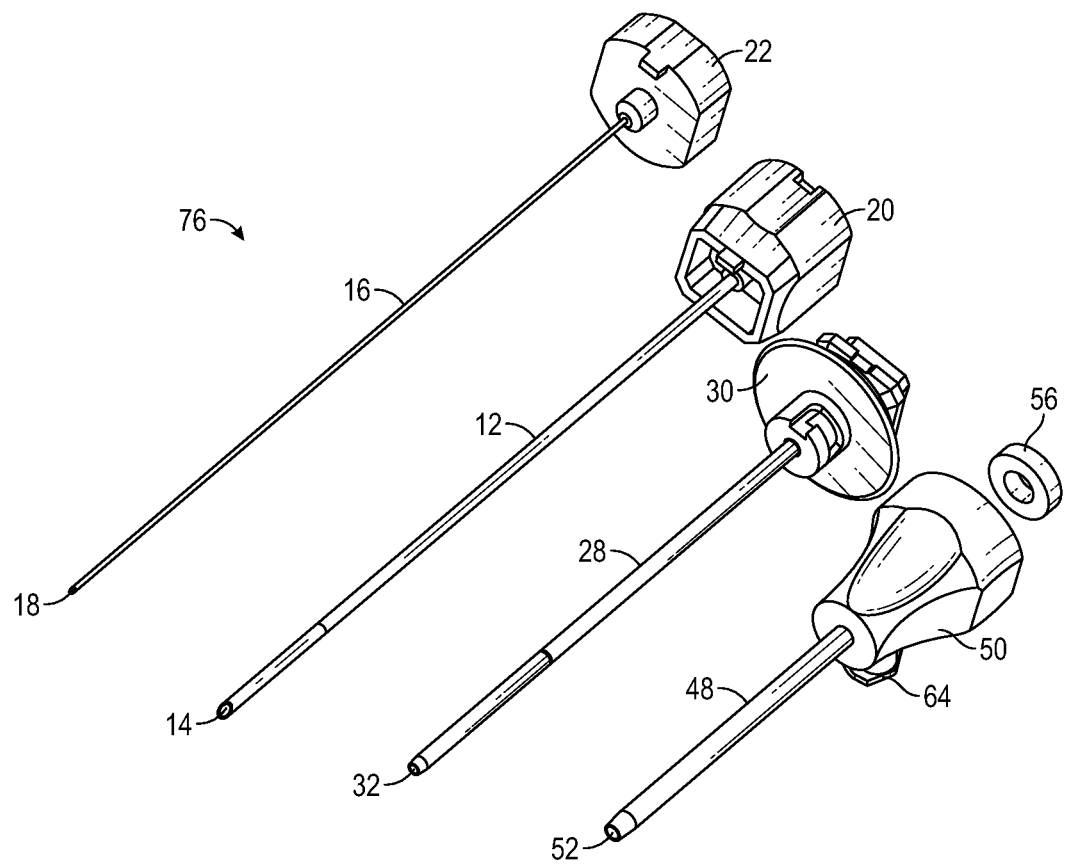
FIG. 22 shows a perspective view of a representative arthroscopic placement assembly in a disassembled or exploded state.
Figure 23:
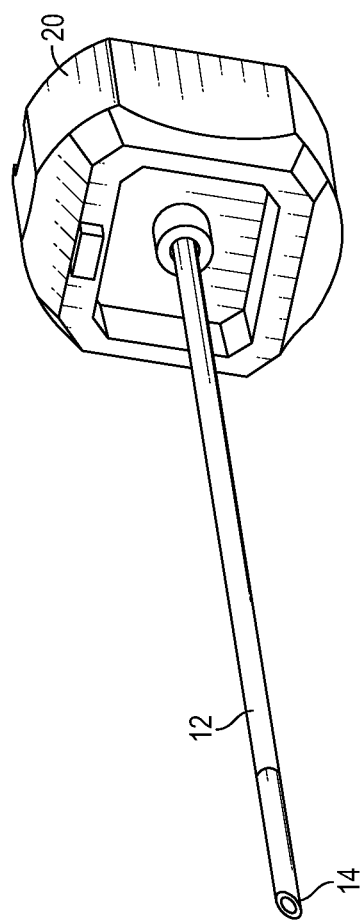
FIG. 23 shows a perspective view of an elongate hollow introducing needle.
Figure 24:
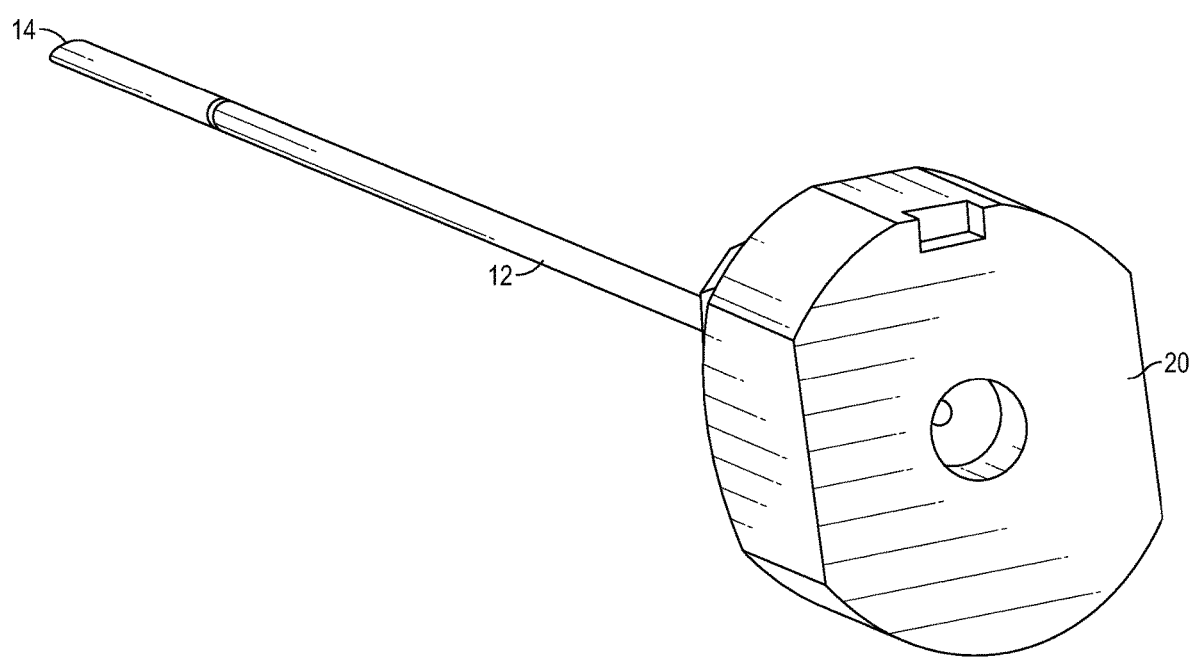
FIG. 24 shows an alternate perspective view of an elongate hollow introducing needle.
Figure 25:
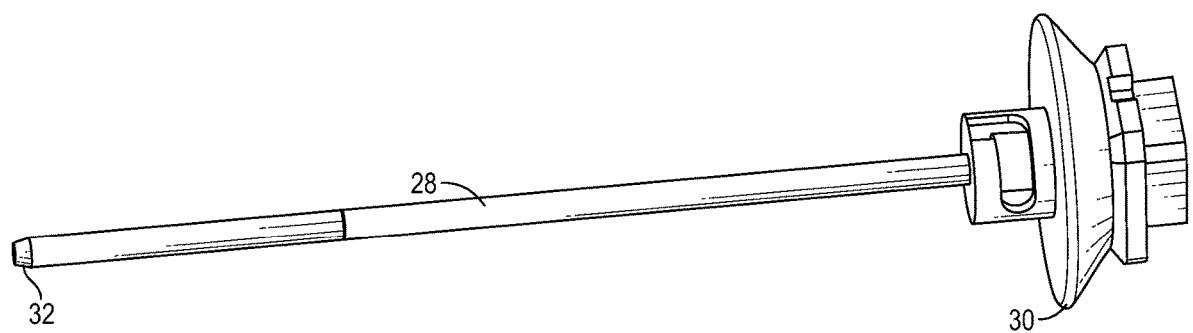
FIG. 25 shows a perspective view of an elongate hollow enlarging shaft.
Figure 26:
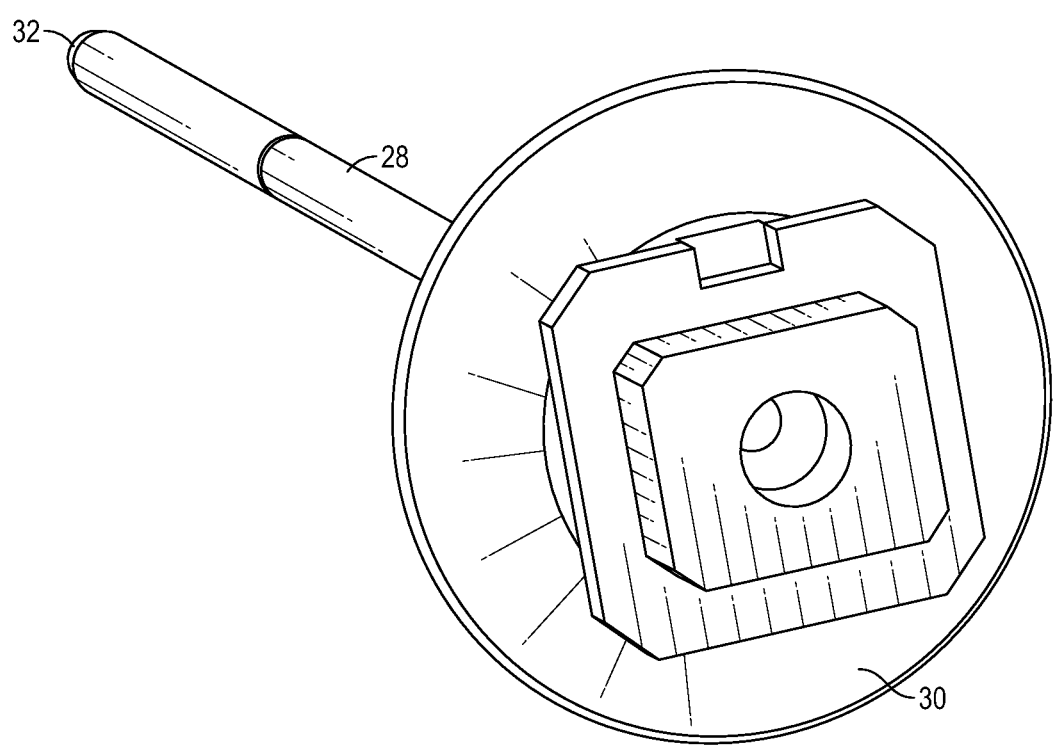
FIG. 26 shows an alternate perspective view of an elongate hollow enlarging shaft.
Figure 27:
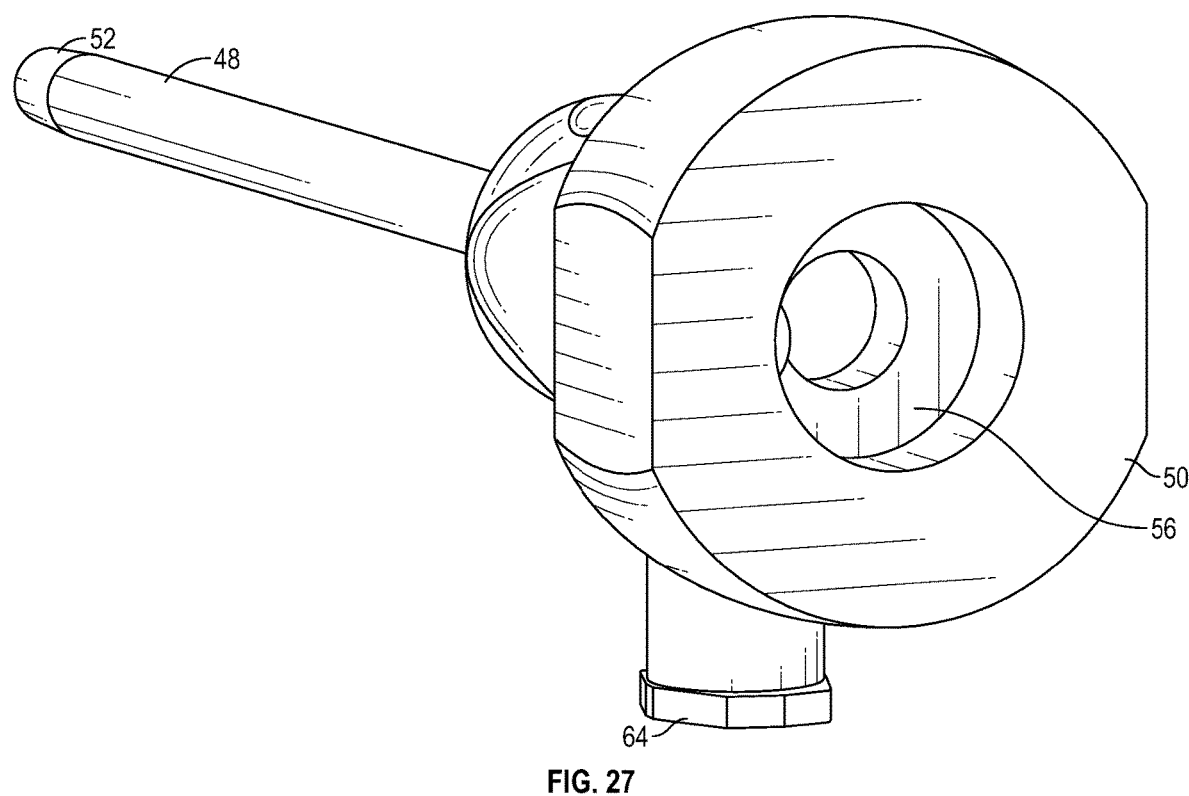
FIG. 27 shows a perspective view of an arthroscopic port sheath.
Figure 28:
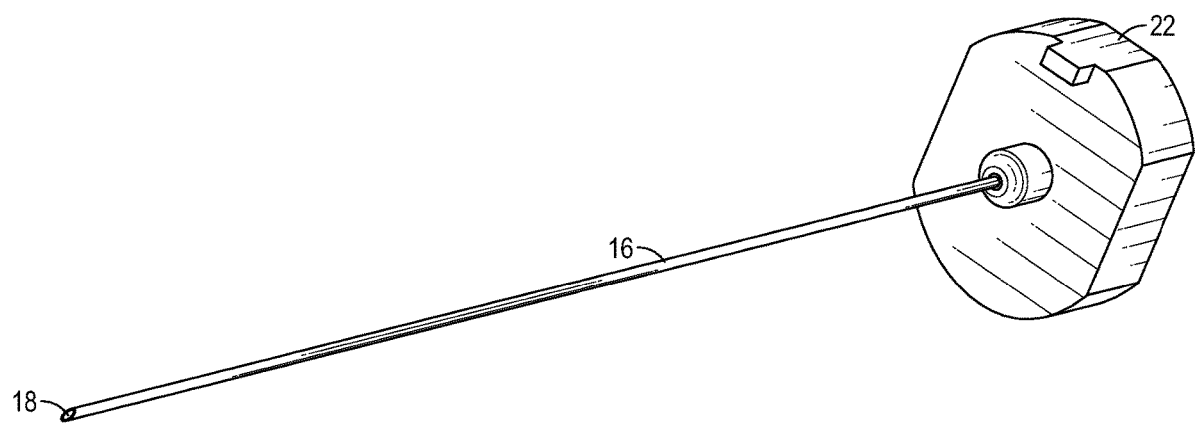
FIG. 28 shows a perspective view of an elongate stylet.

Next, the arthroscopic port sheath 48 is disengaged from the enlarging shaft 28 and advanced, while the enlarging shaft 28 is held steady, until the distal tip 52 is in the joint space. At that point, as shown in FIG. 18, the enlarging shaft 28 is removed and set aside, and the arthroscopic port sheath 48 can be secured in place for use in the arthroscopic procedure. As shown in FIG. 19, an arthroscopic instrument 74 of any desired type is introduced to the joint space through the lumen 62 of the arthroscopic port sheath 48.

FIGS. 20-28 illustrate an alternate embodiment of an arthroscopic placement assembly 76. This assembly 76 also includes an embodiment of the stylet 16, an embodiment of the introducing needle 12, an embodiment of the enlarging shaft 28, and an embodiment of the arthroscopic port sheath 48. The individual features of these components are in many ways similar to the features discussed with respect to the embodiment of the assembly 10 discussed with respect to FIGS. 1-12 and the assembly 66 discussed with respect to FIGS. 13-14. However, the dimensions of the elongate members vary somewhat between the embodiments, and the dimensions and shapes of the various handles 20, 22, 30, and 50 differ between the embodiments. Accordingly, the embodiment of the assembly 66 shown in FIGS. 20-28 serves to illustrate one way in which embodiments may vary while still falling within the scope of the disclosed invention. Additionally, the alternate embodiment lacks the tactile advancement and engagement features between the enlarging shaft 28 and the introducing needle 12 (e.g., the needle mating structure 34 and the shaft mating structure 36) discussed with respect to the embodiment of the assembly 10 shown in FIGS. 1-12, instead utilizing visual cues such as depth markings on the elongate member of the enlarging shaft 28 and/or the relative position of the arthroscopic port sheath 48 to ensure proper depth of penetration thereof.

As may also be seen in FIGS. 20-28, the various engagement structures between the components vary between the components of the assembly 76 and the assembly 10 discussed with respect to FIGS. 1-12. One of ordinary skill in the art will be readily able to discern the workings of these structures from the drawings. Accordingly, a detail description thereof is not included herein.

Figure 29:
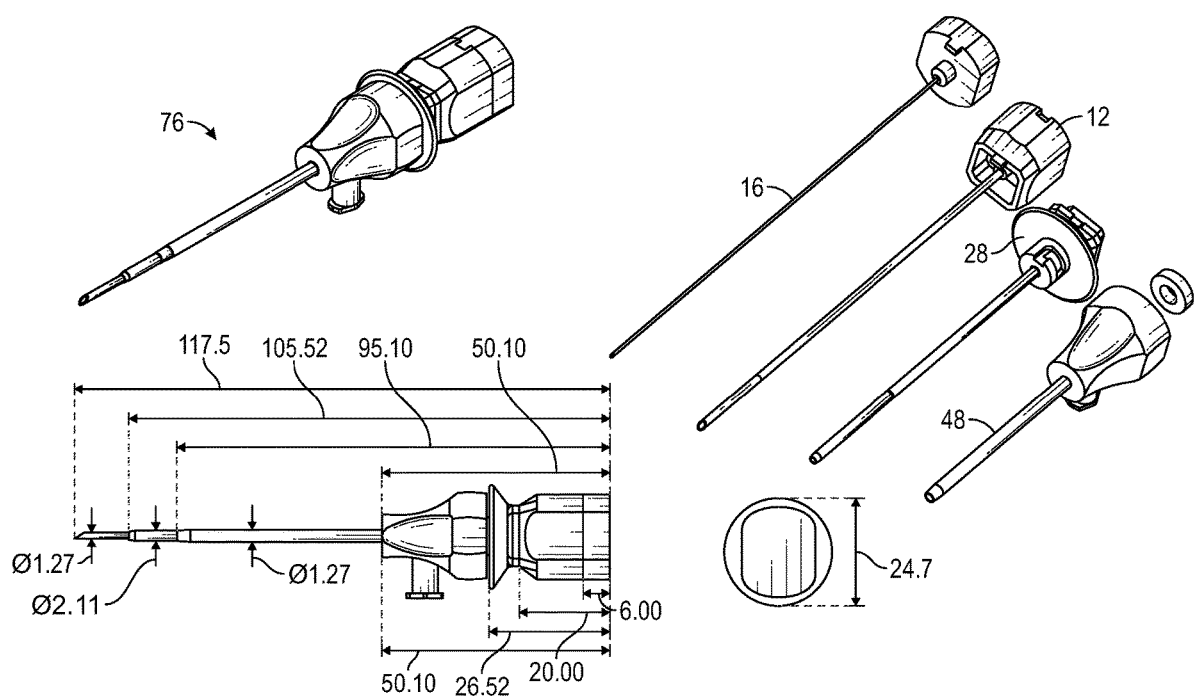
FIG. 29 shows a diagrammatic view of a representative arthroscopic placement assembly in a disassembled state with representative dimensions of parts (in mm) shown.

FIG. 29 shows a schematic representation of the embodiment of the assembly 76 depicted in FIGS. 20-28. In addition, FIG. 29 provides representative dimensions for the various components in mm. In the illustrated embodiment, tolerances for the listed dimensions are as follows: for one decimal place, ±0.5 mm, for two decimal places, ±0.25 mm. However, it should be understood that the provided measurements are intended to be illustrative in all instances, and not restrictive.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. An arthroscopic port introduction system comprising:
    an elongate hollow introducing needle;
    an elongate hollow enlarging shaft adapted to be disposed over the elongate hollow introducing needle such that an operative tissue-penetrating length of the elongate hollow introducing needle is exposed beyond a distal end of the elongate hollow enlarging shaft, and wherein the elongate hollow introducing needle can be removed in a proximal direction from the elongate hollow enlarging shaft; and
    an arthroscopic port sheath adapted to be disposed over the elongate hollow enlarging shaft such that an operative tissue-penetrating length of the elongate hollow enlarging shaft is exposed beyond a distal end of the arthroscopic port sheath,
    wherein the elongate hollow enlarging shaft can be removed in a proximal direction from the arthroscopic port sheath, and
    wherein the arthroscopic port introduction system further comprises at least one of:
        a first handle that extends laterally from a longitudinal axis of the elongate hollow introducing needle at a proximal portion of the elongate hollow introducing needle so as to prevent a distal end of the elongate hollow enlarging shaft from being slid over a proximal end, and being moved towards a distal end, of the elongate hollow introducing needle; and
        a second handle that extends laterally from a longitudinal axis of the elongate hollow enlarging shaft at a proximal end of the elongate hollow enlarging shaft so as to prevent a distal end of the arthroscopic port sheath from being slid over a proximal end, and being moved towards a distal end, of the elongate hollow enlarging shaft.

2. The arthroscopic port introduction system as recited in claim 1, wherein the arthroscopic port sheath comprises a main lumen and a side port.

3. The arthroscopic port introduction system as recited in claim 1, further comprising an elongate stylet sized and adapted to be disposed within the elongate hollow introducing needle, wherein the elongate stylet comprises a stylet handle that extends laterally from a longitudinal axis of the elongate stylet and that is adapted to facilitate insertion or withdrawal of the elongate stylet into and from tissue and into and from the elongate hollow introducing needle.

4. The arthroscopic port introduction system as recited in claim 1, wherein the system is adapted to:
    be fully assembled with the operative tissue-penetrating length of the elongate hollow introducing needle protruding distally beyond the distal end of the elongate hollow enlarging shaft and the operative tissue-penetrating length of the elongate hollow enlarging shaft protruding distally beyond the distal end of the arthroscopic port sheath;
    have the distal end of the elongate hollow introducing needle be inserted into an arthroscopic space such that the elongate hollow introducing needle is inserted into tissue up to a maximum of the operative tissue-penetrating length of the elongate hollow introducing needle;
    without withdrawing the elongate hollow introducing needle from the arthroscopic space, have the distal end of the elongate hollow enlarging shaft be advanced into the arthroscopic space such that the elongate hollow enlarging shaft is inserted into tissue up to a maximum of the operative tissue-penetrating length of the elongate hollow enlarging shaft;
    without withdrawing the elongate hollow enlarging shaft from the arthroscopic space, have the distal end of the arthroscopic port sheath be advanced into the arthroscopic space through tissue along a path occupied by the elongate hollow enlarging shaft; and
    without withdrawing the arthroscopic port sheath, withdraw the elongate hollow introducing needle and withdraw the elongate hollow enlarging shaft proximally from within the arthroscopic port sheath, thereby creating an open passage through the arthroscopic port sheath from a location exterior to a patient body to the arthroscopic space to permit passage of an arthroscopic instrument therethrough.

5. The arthroscopic port introduction system as recited in claim 1, further comprising a needle mating structure that is configured to allow the elongate hollow enlarging shaft to move between, and be selectively retained in, a first position and a second position with respect to the elongate hollow introducing needle, with the first position being disposed proximate to the second position on the elongate hollow introducing needle.

6. The arthroscopic port introduction system as recited in claim 5, wherein the needle mating structure comprises a first circumferential guide and a second circumferential guide.

7. The arthroscopic port introduction system as recited in claim 1 further comprising at least one of:
   a first coupling mechanism that is configured to extend between the elongate hollow introducing needle and the elongate hollow enlarging shaft to selectively lock a rotation of the elongate hollow introducing needle to a rotation of the elongate hollow enlarging shaft; and
   a second coupling mechanism that is configured to extend between the elongate hollow enlarging shaft and the arthroscopic port sheath to selectively lock the rotation of the elongate hollow enlarging shaft to a rotation of the arthroscopic port sheath.

8. The arthroscopic port introduction system as recited in claim 1, wherein the arthroscopic port introduction system comprises at least one of:
   a first coupling mechanism that is configured to extend between the elongate hollow introducing needle and the elongate hollow enlarging shaft to selectively lock a rotation of the elongate hollow introducing needle to a rotation of the elongate hollow enlarging shaft; and
   a second coupling mechanism that is configured to extend between the elongate hollow enlarging shaft and the arthroscopic port sheath to selectively lock the rotation of the elongate hollow enlarging shaft to a rotation of the arthroscopic port sheath.

9. The arthroscopic port introduction system as recited in claim 1, wherein the distal end of the elongate hollow enlarging shaft and the distal end of the arthroscopic port sheath each comprise a beveled tip.

10. The arthroscopic port introduction system as recited in claim 1, wherein:
    the elongate hollow introducing needle comprises an outer diameter;
    the elongate hollow enlarging shaft comprises an inner diameter slightly larger than the outer diameter of the elongate hollow introducing needle, such that the elongate hollow introducing needle can move within the elongate hollow enlarging shaft smoothly and easily, but without significant lateral play;
    the elongate hollow enlarging shaft comprises an outer diameter; and
    the arthroscopic port sheath comprises an inner diameter slightly larger than the outer diameter of the elongate hollow enlarging shaft, such that the elongate hollow enlarging shaft can move within the arthroscopic port sheath smoothly and easily, but without significant lateral play.

11. The arthroscopic port introduction system as recited in claim 1, further comprising a seal that adapted to be disposed between the proximal end of the elongate hollow enlarging shaft and a portion of the elongate hollow introducing needle.

12. The arthroscopic port introduction system as recited in claim 1, wherein each of the elongate hollow introducing needle, the elongate hollow enlarging shaft, and the arthroscopic port sheath comprise a penetration depth marking spaced from the respective distal ends thereof to guide a depth of placement of the elongate hollow introducing needle, of the elongate hollow enlarging shaft, and of the arthroscopic port sheath within an arthroscopic space.

13. The arthroscopic port introduction system as recited in claim 12, wherein the penetration depth markings are respectively visible on a distal exterior surface of each of the elongate hollow introducing needle, the elongate hollow enlarging shaft, and the arthroscopic port sheath.

14. The arthroscopic port introduction system of claim 1, further comprising one or more additional elongate hollow enlarging shafts concentrically disposed about the elongate hollow enlarging shaft recited in claim 1 and within the arthroscopic port sheath.

15. An arthroscopic port introduction system comprising:
    an elongate hollow introducing needle;
    an elongate hollow enlarging shaft adapted to be disposed over the elongate hollow introducing needle whereby an operative tissue-penetrating length of the elongate hollow introducing needle is exposed beyond a distal end of the elongate hollow enlarging shaft, and wherein the elongate hollow introducing needle can be removed in a proximal direction from the elongate hollow enlarging shaft; and
    an arthroscopic port sheath adapted to be disposed over the elongate hollow enlarging shaft whereby an operative tissue-penetrating length of the elongate hollow enlarging shaft is exposed beyond a distal end of the arthroscopic port sheath,
    wherein the elongate hollow enlarging shaft can be removed in a proximal direction from the arthroscopic port sheath, and
    wherein the arthroscopic port introduction system comprises a needle mating structure that allows the elongate hollow enlarging shaft to move between, and be selectively retained in, a first position and a second position with respect to the elongate hollow introducing needle, with the first position being disposed proximate to the second position on the elongate hollow introducing needle.

16. The arthroscopic port introduction system as recited in claim 15, further comprising at least one of:
    a first coupling mechanism that is configured to selectively lock a rotation of the elongate hollow introducing needle to a rotation of the elongate hollow enlarging shaft; and
    a second coupling mechanism that is configured to selectively lock the rotation of the elongate hollow enlarging shaft to a rotation of the arthroscopic port sheath.

17. The arthroscopic port introduction system as recited in claim 15, wherein the arthroscopic port sheath comprises:
    a main lumen that extends into the arthroscopic port sheath from a proximal end of the arthroscopic port sheath; and
    a side port that extends into the arthroscopic port sheath from a lateral side of the arthroscopic port sheath.

18. The arthroscopic port introduction system as recited in claim 15, further comprising at least one of:
    a first handle that extends laterally from a longitudinal axis of the elongate hollow introducing needle at a proximal portion of the elongate hollow introducing needle; and
    a second handle that extends laterally from a longitudinal axis of the elongate hollow enlarging shaft at a proximal end of the elongate hollow enlarging shaft.

19. An arthroscopic port introduction system comprising:
    an elongate hollow introducing needle;

an elongate hollow enlarging shaft adapted to be disposed over the elongate hollow introducing needle whereby an operative tissue-penetrating length of the elongate hollow introducing needle is exposed beyond a distal end of the elongate hollow enlarging shaft, and wherein the elongate hollow introducing needle can be removed in a proximal direction from the elongate hollow enlarging shaft; and an arthroscopic port sheath adapted to be disposed over the elongate hollow enlarging shaft whereby an operative tissue-penetrating length of the elongate hollow enlarging shaft is exposed beyond a distal end of the arthroscopic port sheath, wherein the elongate hollow enlarging shaft can be removed in a proximal direction from the arthroscopic port sheath, and wherein the arthroscopic port introduction system comprises at least one of:

a first coupling mechanism that is configured to extend between the elongate hollow introducing needle and the elongate hollow enlarging shaft to selectively lock a rotation of the elongate hollow introducing needle to a rotation of the elongate hollow enlarging shaft; and a second coupling mechanism that is configured to extend between the elongate hollow enlarging shaft and the arthroscopic port sheath to selectively lock the rotation of the elongate hollow enlarging shaft to a rotation of the arthroscopic port sheath.

20. The arthroscopic port introduction system as recited in claim 19, wherein at least one of a distal end of the elongate hollow introducing needle and a distal end of the arthroscopic port sheath comprise a penetration depth marking to guide a depth placement of a portion of the arthroscopic port introduction system.

21. The arthroscopic port introduction system as recited in claim 19, further comprising a needle mating structure that is configured to allow the elongate hollow enlarging shaft to move between, and be selectively retained in, a first position and a second position with respect to the elongate hollow introducing needle, with the first position being disposed proximate to the second position on the elongate hollow introducing needle.

22. The arthroscopic port introduction system as recited in claim 21, wherein the needle mating structure comprises a first circumferential guide and a second circumferential guide.

* * * * *